United States Patent
Kim et al.

(10) Patent No.: US 12,194,048 B2
(45) Date of Patent: Jan. 14, 2025

(54) USE OF PYRROLOPYRIDINE DERIVATIVES FOR PREVENTING OR TREATING INFLAMMATORY DISEASES

(71) Applicant: VORONOI CO., LTD., Incheon (KR)

(72) Inventors: Soo Chan Kim, Gyeonggi Do (KR); Dae Kwon Kim, Daegu (KR); Dong Hyuk Seo, Incheon (KR); Hyun Kyung Kim, Incheon (KR); Sung Hwan Kim, Incheon (KR); Hye Min Hwang, Gyeonggi-do (KR); Ji Eun Choi, Seoul (KR)

(73) Assignee: VORONOI CO., LTD., Incheon (KR)

( * ) Notice: Subject to any disclaimer, the term of this patent is extended or adjusted under 35 U.S.C. 154(b) by 0 days.

(21) Appl. No.: 18/486,783

(22) Filed: Oct. 13, 2023

(65) Prior Publication Data

US 2024/0180918 A1    Jun. 6, 2024

Related U.S. Application Data

(63) Continuation of application No. 17/643,554, filed on Dec. 9, 2021, now abandoned.

(30) Foreign Application Priority Data

Dec. 9, 2020 (KR) .................. 10-2020-0171340

(51) Int. Cl.
*A61K 31/5377* (2006.01)
*A61K 45/06* (2006.01)
(Continued)

(52) U.S. Cl.
CPC .......... *A61K 31/5377* (2013.01); *A61K 45/06* (2013.01); *A61P 1/00* (2018.01);
(Continued)

(58) Field of Classification Search
CPC ....... A61K 31/5377; A61K 45/06; A61P 1/00; A61P 17/00; A61P 17/06; A61P 19/02; A61P 29/00; A61P 1/04
(Continued)

(56) References Cited

U.S. PATENT DOCUMENTS

| | | |
|---|---|---|
| 11,117,892 B2 | 9/2021 | Choi et al. |
| 2014/0066406 A1 | 3/2014 | Wang et al. |
| 2020/0207756 A1 | 7/2020 | Choi et al. |

FOREIGN PATENT DOCUMENTS

| | | |
|---|---|---|
| CN | 102105150 A | 6/2011 |
| CN | 105940004 A | 9/2016 |

(Continued)

OTHER PUBLICATIONS

"Encyclopedia of Chinese Medicine", Chinese Medical Encyclopedia Editorial Committee, Shanghai Science and Technology Press, 1st edition, Oct. 1988, pp. 12-13.
(Continued)

*Primary Examiner* — Taylor V Oh
(74) *Attorney, Agent, or Firm* — Seed IP Law Group LLP

(57) ABSTRACT

The present invention relates to a pharmaceutical composition for preventing and/or treating inflammatory disease, the composition comprising a pyrrolopyridine-derivative compound as an active ingredient; the compound represented by Chemical Formula 1 according to the present invention, enantiomers thereof or pharmaceutically acceptable salts thereof, which have excellent inhibitory activity against not only protein kinases but also inflammatory factors and inflammatory cytokines; therefore a pharmaceutical composition comprising the same as an active ingredient may be useful in prevention, treatment and/or improvement of inflammatory disease, in particular but not limited to inflammatory bowel disease, rheumatoid arthritis, or lupus.

39 Claims, 18 Drawing Sheets

(51) Int. Cl.
- A61P 1/00 (2006.01)
- A61P 17/00 (2006.01)
- A61P 17/06 (2006.01)
- A61P 19/02 (2006.01)

(52) U.S. Cl.
CPC .............. *A61P 17/00* (2018.01); *A61P 17/06* (2018.01); *A61P 19/02* (2018.01)

(58) Field of Classification Search
USPC ...................................................... 514/234.5
See application file for complete search history.

(56) References Cited

FOREIGN PATENT DOCUMENTS

| | | |
|---|---|---|
| CN | 105980388 A | 9/2016 |
| CN | 107801397 A | 3/2018 |
| JP | 2011518219 A | 6/2011 |
| KR | 10-2013-0121122 A | 11/2013 |
| KR | 10-2014-0040715 A | 4/2014 |
| KR | 10-2016-0106623 A | 9/2016 |
| KR | 10-2017-0058465 A | 5/2017 |
| KR | 10-2017-0106452 A | 9/2017 |
| KR | 10-2018-0015142 A | 2/2018 |
| KR | 10-2018-0097162 A | 8/2018 |
| KR | 101896568 B1 | 9/2018 |
| KR | 10-2018-0132882 A | 12/2018 |
| RU | 2434013 C2 | 11/2011 |
| WO | WO-2006127587 A1 | 11/2006 |
| WO | WO-2008129152 A1 | 10/2008 |
| WO | WO-2009032694 A1 | 3/2009 |
| WO | WO-2009032703 A1 | 3/2009 |
| WO | WO-2009131687 A2 | 10/2009 |
| WO | WO-2011090738 A2 | 7/2011 |
| WO | WO-2012135631 A1 | 10/2012 |
| WO | WO-2014170248 A1 | 10/2014 |
| WO | WO-2015113451 A1 | 8/2015 |
| WO | WO-2015113452 A1 | 8/2015 |
| WO | WO-2016130920 A2 | 8/2016 |
| WO | WO-2016195776 A1 | 12/2016 |
| WO | WO-2018155916 A2 | 8/2018 |
| WO | WO-2018174650 A1 | 9/2018 |
| WO | WO-2020149715 A1 | 7/2020 |
| WO | WO-2020149723 A1 | 7/2020 |
| WO | WO-2020232332 A1 | 11/2020 |
| WO | WO-2020235973 A1 | 11/2020 |
| WO | WO-2022123311 A1 | 6/2022 |

OTHER PUBLICATIONS

"The Organic Chemistry of Drug Design and Drug Action", edited by Richard B. Silverman, Jan. 31, 2008.
Berge et al., "Pharmaceutical salts," J Pharm Sci. 1977;66(1):1-19.
Brand et al., "Collagen-induced arthritis," Nat. Protoc. 2007;2(5):1269-75.
Chan et al., "Discovery of a Highly Selective, Brain-Penetrant Aminopyrazole LRRK2 Inhibitor." ACS Med Chem Lett. 2012;4(1):85-90.
Coussens and Werb, "Inflammation and cancer," Nature. 2002;420(6917):860-7.
Coxon et al., "Cyclin-Dependent Kinase (CDK) Inhibitors: Structure-Activity Relationships and Insights into the CDK-2 Selectivity of 6-Substituted 2-Arylaminopurines", J Med Chem. Mar. 9, 2017;60(5):1746-1767.
Ding et al., "Discovery of 4-ethoxy-7H-pyrrolo[2,3-d]pyrimidin-2-amines as potent, selective and orally bioavailable LRRK2 inhibitors." Bioorg Med Chem Lett. 2018;28(9):1615-1620.
Dirice et al. "Inhibition of DYRK1A Stimulates Human ß-Cell Proliferation." Diabetes. 2016;65(6):1660-71.
Extended European Search Report for corresponding European Application No. EP18770572 dated Nov. 17, 2020.
Hatcher et al., "Discovery of a Pyrrolopyrimidine (JH-II-127), a Highly Potent, Selective, and Brain Penetrant LRRK2 Inhibitor", ACS Med Chem Lett. Apr. 7, 2015;6(5):584-9.
International Search Report of PCT/KR2018/003459 dated Mar. 23, 2018.
Iragavarapu. Journal of Hematology & Oncology, 2015, 8:17, 1-9 (Year: 2015).
Kimura et al., "The DYRK1A gene, encoded in chromosome 21 Down syndrome critical region, bridges between beta-amyloid production and tau phosphorylation in Alzheimer disease." Hum Mol Genet. 2007; 16(1):15-23 (1), 15-23.
Kinney et al., "Inflammation as a central mechanism in Alzheimer's disease," Alzheimers Dement (NY). 2018;4:575-590.
Kruczynski. Expert Opinion on Therapeutic Targets, 2012, 16(11), 1127-38 (Year: 2012).
Kwiatkowski et al., "Small Molecule Kinase Inhibitors Provide Insight into Mps1 Cell Cycle Function", Nat Chem Biol. 2010; 6(5):359-68.
Lee et al., "Small-molecule EGFR tyrosine kinase inhibitors for the treatment of cancer." Expert Opin Investig Drugs. 2014;23(10):1333-48.
Li et al., "DYRK1A inhibition suppresses STAT3/EGFR/Met signalling and sensitizes EGFR wild-type NSCLC cells to AZD9291." J Cell Mol Med. 2019;23(11):7427-7437.
Lobaugh et al., Piracetam Therapy Does Not Enhance Cognitive Functioning in Children with Down Syndrome, Arch Pediatr Adoles Med. 2001; 155 442-448.
Michellys, et al., Design and synthesis of novel selective anaplastic lymphoma kinase inhibitors, Bioorganic & Medicinal Chemistry Letters 26 (2016) 1090-1096.
Mojzych et al., "Synthesis and kinase inhibitory activity of new sulfonamide derivatives of pyrazolo[4,3-e][1,2,4]triazines." Eur J Med Chem. 2014;78:217-24.
PCT International Preliminary Report on Patentability from PCT/IB2021/000857, Jun. 13, 2023.
PCT International Search Report and Written Opinion from PCT/IB2021/000857 dated Apr. 11, 2022.
PCT International Search Report and Written Opinion from PCT/KR2020/000944 dated May 6, 2020.
PCT International Search Report and Written Opinion from PCT/KR2020/000960 dated May 1, 2020.
PCT International Search Report and Written Opinion from PCT/KR2020/006730 dated Sep. 4, 2020.
Pine et al., "Inflammation and bone erosion are suppressed in models of rheumatoid arthritis following treatment with a novel Syk inhibitor." Clin Immunol. 2007; 124(3):244-57.
Seo et al., "P001 The novel DYRK1a inhibitor VRN024219 alleviates disease severity on the IBD mouse models by modulating T-cell differentiation," J Crohns Colitis. 2020; 14(suppl 1):S129.
Shackelford et al., "Qualitative and quantitative analysis of non-neoplastic lesions in toxicology studies." Toxicol Pathol. 2002;30(1):93-6.
Wegiel et al., "The role of DYRK1A in neurodegenerative diseases." Febs J. 2011;278(2):236-4.
Williamson et al., "Design of Leucine-Rich Repeat Kinase 2 (LRRK2) Inhibitors Using a Crystallographic Surrogate Derived from Checkpoint Kinase 1 (CHK1)." J Med Chem. 2017;60(21):8945-8962.
Qidong You, Medicinal Chemistry, Chemical Industry Press, Jan. 2004, pp. 32-33, and English translation of article.
Extended European Search Report, dated Sep. 9, 2024, for European Patent Application No. 201902773-1109. (10 pages).
Lee et al., "The novel DYRKIA inhibitor KVN93 regulates cognitive function, amyloid-beta pathology, and neuroinflammation," *Free Radical Biology and Medicine* 160:575-595, Nov. 20, 2020. (21 pages).

USE OF PYRROLOPYRIDINE DERIVATIVES FOR PREVENTING OR TREATING INFLAMMATORY DISEASES

RELATED APPLICATIONS AND INCORPORATION BY REFERENCE

This application is a continuation of U.S. application Ser. No. 17/643,554, filed Dec. 9, 2021, which claims priority to Korean Application No. 10-2020-0171340, filed Dec. 9, 2020, the entire disclosure of which is hereby incorporated by reference.

TECHNICAL FIELD OF THE INVENTION

The present invention relates to a novel use of pyrrolopyridine derivative compounds for preventing and/or treating inflammatory diseases.

BACKGROUND OF THE INVENTION

Pyrrolopyridine derivatives are bicyclic compounds wherein pyridine and pyrrole are bonded and used for various pharmaceutical purposes. Accordingly, various pyrrolopyridine derivatives have been synthesized. Patent literature which discloses pyrrolopyridine derivatives include Korean Laid-open Patent Nos. 10-2018-0015142, 10-2017-0106452, and 10-2017-0058465.

In most of the above patent literature, it can be known that pyrrolopyridine derivatives are used as inhibitors for protein kinases. Accordingly, the inventors set out to identify other physiological activities and pharmacological mechanisms of the pyrrolopyridine derivatives.

Inflammation is the mechanism by which living tissue that has been damaged by physical action, chemical substance, or bacterial infection is restored. When said stimuli are applied, vasoactive substances such as histamine, serotonin, and prostaglandin are released, increasing vascular permeability and causing inflammation.

It has been reported that when macrophages are activated by lipopolysaccharides (LPS), the TLR (toll-like receptor)-4 signal pathway including phosphorylation of mitogen-activated protein kinase (MAPK) and activation of transcription factor NF-κB (nuclear factor-kappa B) is initiated, which induces the generation of inflammation-related factors such as NO, IL-6, IL-1β, TNF-α, iNOS and COX-2 (Chae HS, et al. Biol Pharm Bull. 2009:32(4): 553-557.).

Recently, there has been active research into methods of reducing inflammation generation, and nonsteroidal anti-inflammatory drugs (NSAIDs) including bradykinin antagonists and TNF-α inhibitors having anti-inflammatory, analgesic, and antipyretic actions are commonly used as anti-inflammatory drugs. However, long-term use of nonsteroidal anti-inflammatory drugs may cause gastrointestinal disorders, and serious side effects such as secondary anemia, asthma, suppression of labor induction, adverse effects on the kidneys, liver damage, and hypersensitivity have been reported.

Therefore, there is a need for the development of an anti-inflammatory agent which minimizes the usual and often seen side effects of currently known anti-inflammatory agents, does not harm the human body especially for maintenance use, and can be administered over an extended period of time.

Thereupon, the present inventors discovered that pyrrolopyridine derivatives inhibit the expression of inflammation-related factors including inflammatory cytokines such as NO, IL-6, IL-1β, TNF-α and the like, and by confirming in-vivo stability and safety of the same, have identified potential for the use of pyrrolopyridine derivatives as pharmaceutical agents for the prevention and/or treatment of inflammatory diseases.

SUMMARY OF THE INVENTION

A purpose of the present invention is to provide a pharmaceutical composition for prevention and/or treatment of inflammatory diseases, the composition comprising a pyrrolopyridine-derivative compound as an active ingredient.

Another purpose of the present invention is to provide a method for preventing and/or treating inflammatory diseases by administering an effective dose of a pyrrolopyridine-derivative compound to a subject.

Yet another purpose of the present invention is to provide a pyrrolopyridine-derivative composition for prevention and/or treatment of inflammatory disease, and a use for a pharmaceutical composition comprising the same as an active ingredient.

In one embodiment, the present invention provides a method of preventing and/or treating an inflammatory disease in a patient in need thereof, the method comprising administering to the patient a compound represented by Chemical Formula 1:

[Chemical Formula 1]

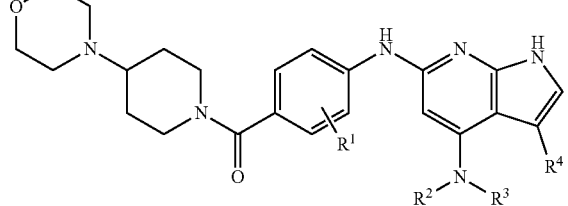

or an isomer, pharmaceutically acceptable salt, or pharmaceutical composition thereof, wherein:
$R^1$ is $C_1$-$C_3$ alkoxy;
$R^2$ and $R^3$ are each independently hydrogen, straight-chain or branched $C_1$-$C_{10}$ alkyl, or $C_3$-$C_6$ cycloalkyl; and
$R^4$ is haloalkyl.

In one embodiment, the present invention provides a method for preventing and/or treating inflammatory diseases, the method comprising a step of administering an effective dose of a pharmaceutical composition comprising a compound represented by Chemical Formula 1, or an isomer or pharmaceutically acceptable salt thereof.

The present invention provides a use of a compound represented by Chemical Formula 1, an isomer thereof, a pharmaceutically acceptable salt thereof, or a pharmaceutical composition comprising the same as an active ingredient, for preventing and/or treating inflammatory diseases.

A compound represented by Chemical Formula 1 according to the present invention, or isomers or pharmaceutically acceptable salts thereof, has excellent inhibitory activity with regard to various protein kinases including DYRK1A, CLK and the like, and/or excellent inhibitory activity against inflammation-related factors, while having excellent in-vivo stability, and a pharmaceutical composition comprising the same as an active ingredient can be useful in treating and/or preventing inflammatory diseases. In particular embodiments, a compound of Chemical Formula 1 can be used for the prevention, treatment, and/or improvement of inflammatory bowel disease, psoriasis, rheumatoid arthritis, and lupus.

DETAILED DESCRIPTION OF CERTAIN EMBODIMENTS

Figure 1A:
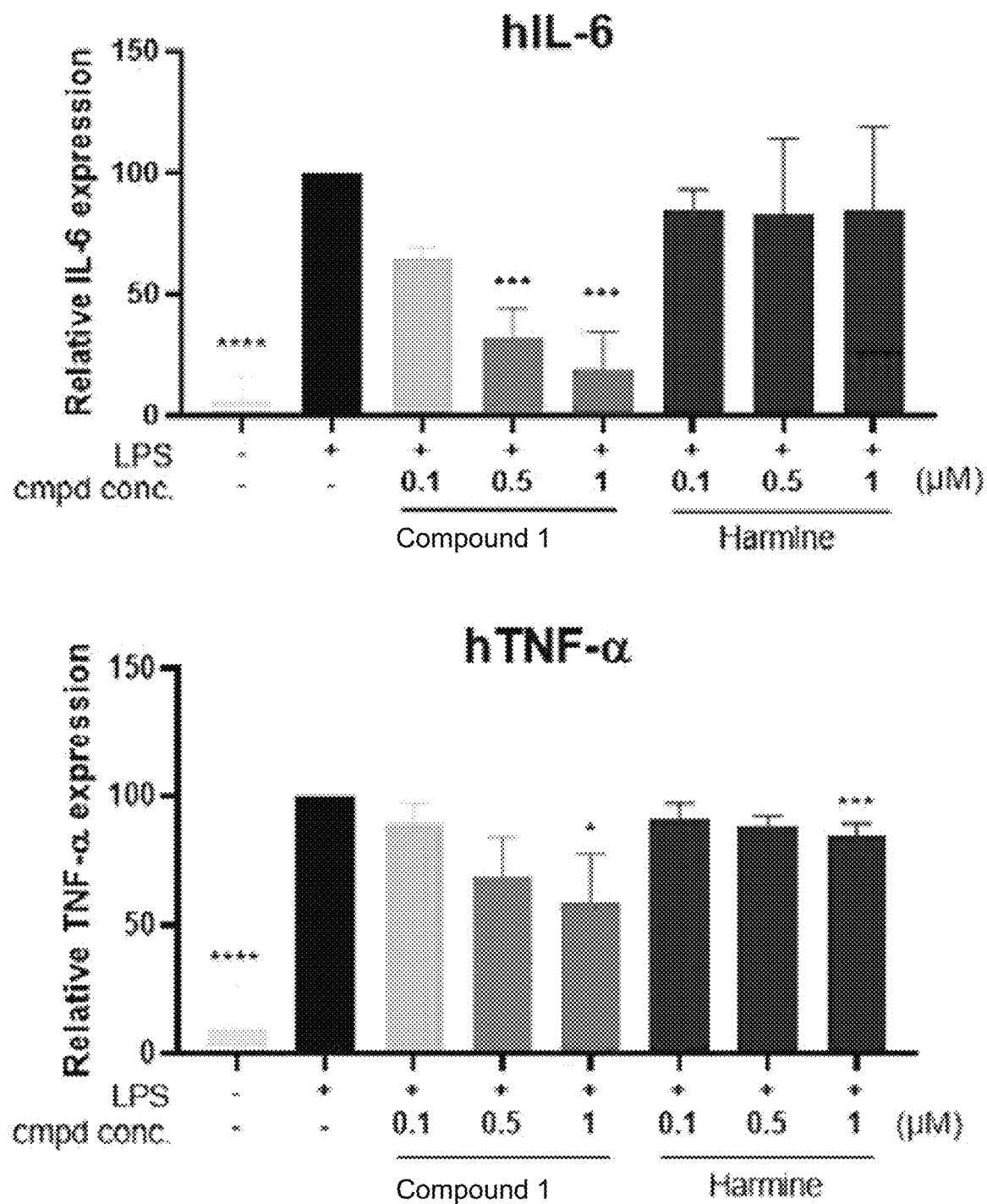
FIG. 1a and FIG. 1b show inhibitory activity against expression of the pro-inflammatory cytokines TNF-α and IL-6 when LPS-stimulated THP-1 cells are treated with Compound 1 (FIG. 1a) and inhibitory activity against intranuclear mobility of p50 and p65 involved in the NF-κb signaling pathway (FIG. 1b).

1. General Description of Certain Embodiments of the Invention

Examples of the present invention may be modified into various different forms, and the scope of the present invention is not limited to the examples described in the following. Furthermore, the examples of the present invention are provided to more completely describe the present invention to a person having ordinary skill in the art. Additionally, in the entirety of the specification, "comprising" an element, unless specifically stated otherwise, does not exclude other elements and means that other elements may be further comprised.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As used herein, the term "administration" refers to using a suitable method to introduce the pharmaceutical composition of the present invention to a subject suspected to have inflammatory disease, and administration may be performed through various pathways so long as the target tissue can be reached.

As used herein, the term "alkyl" may mean a straight-chain or branched acyclic saturated hydrocarbon consisting of carbon atoms. Representative —($C_{1-8}$alkyl) may include methyl, ethyl, n-propyl, n-butyl, n-pentyl, n-hexyl, n-heptyl and n-octyl; and branched chain saturated alkyls may include isopropyl, sec-butyl, isobutyl, tert-butyl, isopentyl, 2-methylpentyl, 3-methylpentyl, 4-methylpentyl, 2,3-dimethylbutyl, and the like. The $C_{1-8}$ alkyl may be substituted or unsubstituted. For example, a $C_{1-8}$ alkyl group may be substituted with a phenyl to form a benzyl group.

As used herein, the phrase "conjointly administering" refers herein to any form of administration of two or more different therapeutic compounds such that the second administered compound is administered while the first administered therapeutic compound is still effective in the body (e.g., the two compounds are simultaneously effective in the patient, which may include additive or synergistic effects of the two compounds).

As used herein, the term "cycloalkyl" may refer to a nonaromatic saturated or unsaturated carbon ring. Representative cycloalkyls include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl and cyclooctadienyl. The cycloalkyl group may be substituted or unsubstituted. In one embodiment, the cycloalkyl group may be a $C_{3-8}$ cycloalkyl group. A cycloalkyl group of $C_7$ or greater may have two or more cyclic structures, and a specific example thereof may be a bicycloalkyl group, and more specifically, bicycloheptane may be used in the present invention.

At least one of the homogenous or heterogeneous substituents mentioned in the above may be substituted in like positions or different positions, and may also be sequentially substituted. The term "sequentially" in the above refers to one substituent being substituted in a chemical formula followed by the consecutive substitution of another substituent, and, for example, in a case wherein an alkyl group is substituted, and then a cycloalkyl is substituted at the alkyl group, and a carbonyl group is sequentially substituted at the cycloalkyl group, the compound may be named carbonylcycloalkylalkyl to indicate it has been sequentially substituted.

As used herein, the term "halogen" may be F, Cl, Br or I.

As used herein, the term "haloalkyl" may refer to a straight chain or branched chain alkyl (hydrocarbon) having a carbon atom substituted by at least one halogen atom. Examples of haloalkyl include, but are not limited to, methyl, ethyl, propyl, isopropyl, isobutyl and N-butyl independently substituted by at least one halogen atom, for example, F, Cl, Br or I.

As used herein, the term "hydrate" refers to a compound of the present invention or a salt thereof, comprising a stoichiometric or non-stoichiometric amount of water bonded by a non-covalent intermolecular force. The hydrate of the compound represented by Formula 1 of the present invention may include a stoichiometric or non-stoichiometric amount of water that is bound by non-covalent intermolecular forces. Such hydrates may comprise at least one equivalent, and preferably 1 to 5 equivalents, of water. Such hydrates may be prepared by crystallizing, from water or a solvent comprising water, a compound represented by Chemical Formula 1 of the present invention, an isomer thereof, or pharmaceutically acceptable salts thereof.

As used herein, the term "isomer" refers to a compound of the present invention or a salt thereof that has the same chemical formula or molecular formula but differs structurally or sterically. Included in such isomers are all structural isomers such as tautomers, R or S isomers, stereoisomers such as geometrical isomers (trans, cis), and enantiomers. All such isomers and compounds thereof are too included in the scope of the present invention. Unless otherwise specified, a solid line bond (—) connected to an asymmetric carbon atom may include a solid wedge bond (/) or dashed wedge bond (/) representing the absolute arrangement of a stereogenic center.

As used herein, the term "inflammatory disease" is a term generally referring to diseases whose principal condition is inflammation, and specifically, but not limited to, may be one selected from asthma, acute lung injury, GvHD Graft versus Host Disease), chronic obstructive pulmonary disease, allergy, systemic lupus erythematosus, scleroderma, inflammatory bowel disease (for example ulcerative colitis and Crohn's disease), atopic dermatitis, psoriasis, anaphylaxis, dermatitis, diabetic retinosis, retinitis, macular degeneration, uveitis, conjunctivitis, rheumatoid arthritis, ankylosing spondylitis, osteoarthritis, osteoporosis, diabetes, diabetic kidney disease, nephritis, Sjogren's syndrome, Crohn's disease, autoimmune pancreatitis, periodontal disease, alopecia areata, graft versus host disease, chronic pelvic inflammatory disease, endometriosis, rhinitis, tonsilitis, otitis media, sore throat, cystitis and chronic prostatitis. Further inflammatory diseases or diseases having an inflammatory component are disclosed herein.

As used herein, the term "pharmaceutically effective dose" refers to a dose sufficient to treat disease with a reasonable benefit/risk ratio applicable to medical treatment, and the level of the effective dose may be determined depending on factors including the type of subject, severity of disease, age, sex, type of disease, activity of the drug, drug sensitivity, duration of administration, administration pathway and excretion rate, duration of therapy and concomitantly used drugs, and other factors known well to the medical art. The compounds or compositions of the present invention may be administered as a single drug or concomitantly with other drugs, such as by conjoint administration, and may be administered sequentially or simultaneously with commercially marketed therapeutic agents. Furthermore, it may be administered as a single dose or multiple doses. It is important to administer a dose capable of achieving the maximum effect with a minimum amount without developing adverse effects in consideration of all of the above factors; the dose may be readily decided by a person of skill in the art. The administration dose of the compound or composition of the present invention may be determined by an expert according to various factors such as patient status, age, sex and complications. As the compound or composition of the present invention has excellent safety, it may be used at above the decided administration dose.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. In some embodiments, the provided compounds are purified in salt form for convenience and/or ease of purification, e.g., using an acidic or basic mobile phase during chromatography. Salts forms of the provided compounds formed during chromatagraphic purification are contemplated herein (e.g., diammonium salts) and are readily apparent to those having skill in the art.

As used herein, the term "solvate" refers to a compound of the present invention or a salt thereof comprising a stoichiometric or non-stoichiometric amount of solvent bonded by a non-covalent intermolecular force. Preferable solvents, therefore, include volatile or non-toxic solvents, and/or solvents suitable for human administration.

As used herein, the term "treatment" or "therapeutic" includes the suppression, delay, identification, alleviation, weakening, limiting, reduction, inhibition, avoidance or healing of illnesses, conditions, disabilities, damage or health problems, or the occurrence or progression/improvement of such statuses and/or symptoms of such statuses. The term "prevention" refers to avoidance or reduction of risk of contracting, experiencing, suffering or having illnesses, conditions, disabilities, damage or health problems, or the occurrence or progression of such statuses and/or symptoms of such statuses. Treatment or prevention of a disease, condition, disorder, injury or health problem may be partial or complete.

3. Description of Exemplary Embodiments

The present invention provides a compound for the prevention and/or treatment of inflammatory diseases, the compound represented by Chemical Formula 1:

[Chemical Formula 1]

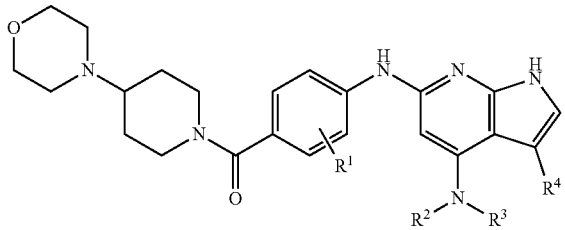

or an isomer, pharmaceutically acceptable salt, or pharmaceutical composition thereof, wherein:
$R^1$ is $C_1$-$C_3$ alkoxy;
$R^2$ and $R^3$ are each independently hydrogen, straight-chain or branched $C_1$-$C_{10}$ alkyl, or $C_3$-$C_6$ cycloalkyl; and
$R^4$ is haloalkyl.

As defined and described herein, $R^1$ is $C_1$-$C_3$ alkoxy.
In some embodiments, $R^1$ is $C_1$-$C_3$ alkoxy. In some embodiments, $R^1$ is methoxy.
In some embodiments, $R^1$ is as found in the compounds of Table 1, below.

As defined and described herein, $R^2$ and $R^3$ are each independently hydrogen, straight-chain or branched $C_1$-$C_{10}$ alkyl, or $C_3$-$C_6$ cycloalkyl.
In some embodiments, $R^2$ is hydrogen. In some embodiments, $R^2$ is a straight-chain $C_1$-$C_{10}$ alkyl. In some embodiments, $R^2$ is a branched $C_1$-$C_{10}$ alkyl. In some embodiments, $R^2$ is a $C_3$-$C_6$ cycloalkyl. In some embodiments, $R^2$ is straight chain or branched chain $C_1$-$C_5$ alkyl or $C_3$-$C_4$ cycloalkyl.
In some embodiments, $R^3$ is hydrogen. In some embodiments, $R^3$ is a straight-chain $C_1$-$C_{10}$ alkyl. In some embodiments, $R^3$ is a branched $C_1$-$C_{10}$ alkyl. In some embodiments, $R^3$ is a $C_3$-$C_6$ cycloalkyl.

In some embodiments, $R^2$ and $R^3$ are as found in the compounds of Table 1, below.
As defined and described herein, $R^4$ is haloalkyl.
In some embodiments, $R^4$ is haloalkyl. In some embodiments, $R^4$ is trifluoromethyl.
In certain embodiments, $R^1$ is methoxy; $R^2$ is straight chain or branched chain $C_1$-$C_5$ alkyl or $C_3$-$C_4$ cycloalkyl; $R^3$ is hydrogen; and $R^4$ is trifluoromethyl.

In certain embodiments, a compound represented by Chemical Formula 1 is (4-((-4-ethylamino)-3-(trifluoromethyl)-1H-pyrrolo[2,3-b]pyridine-6-yl)amino)-3-methoxyphenyl)(4-morpholinopiperidine-1-yl)methanone.

In some embodiments, a compound represented by Chemical Formula 1 is found in Table 1, below.

In some embodiments, a pharmaceutically acceptable salt of a compound represented by Chemical Formula 1 may be interpreted as existing in any form selected from a group comprising any crystalline or amorphous form, or hydrates, solvates or co-crystals thereof.

In some embodiments, a compound of present invention, a pharmaceutically acceptable salt, or a pharmaceutical composition thereof may act as an inhibitor for protein kinase. Furthermore, the compounds mentioned herein may act as inhibitors against inflammation-related factors (e.g., cytokines).

In some embodiments, the protein kinase may be one or more of ALK, ALK (C1156Y), ALK (L1196M), CLK1, CLK2, CLK3, CLK4, CSNK1D, DYRK1A, DYRK1B, DYRK2, GAK, JNK1, LRRK2 (G2019S), LTK, MYLK, PAK2, PHKG1, PHKG2, STK33, ABL1-nonphosphorylated, CAMK2D, CAMKK2, CHEK2, CSNK1A1, CSNK1E, ERK5, HUNK, INSR, JAK1 (JH2domain-pseudokinase), JNK2, JNK3, LRRK2, MAPKAPK2, PLK4, and STK39.

Inflammation-related factors may refer to all factors known to be directly or indirectly associated with inflammatory reaction. In a specific example of the present invention, inflammation-related factors may include pro-inflammatory cytokines, and inflammation-related factors whose activity is inhibited by the compound of the present invention and thereby exhibit preventive and/or therapeutic effects against inflammation may be, for example, selected from one or more of NO, IFN-γ, IL-1α, IL-1β, IL-4, IL-6, IL-10, IL-12, IL-13, IL-17, IL-17A, IL-22, IL-23, IL-33, KC, MIP-1a, MIP-1b, GM-CSF, and TNF-α.

In some embodiments, the present invention provides a method of reducing pro-inflammatory cytokines in a patient in need thereof, the method comprising administering an effective dose of a compound represented by Chemical Formula 1 or an isomer, pharmaceutically acceptable salt, or a pharmaceutical composition thereof to a patient. In some embodiments, the method of reducing pro-inflammatory cytokines reduces one or more of NO, IFN-γ, IL-1α, IL-1β, IL-4, IL-6, IL-10, IL-12, IL-13, IL-17, IL-17A, IL-22, IL-23, IL-33, KC, MIP-1a, MIP-1b, GM-CSF, and TNF-α. In certain embodiments, the method of reducing pro-inflammatory cytokines reduces one or more of IL-6, IL-17A, and TNR-α. In certain embodiments, the method of reducing pro-inflammatory cytokines reduces one or more of IL-4, IL-6, MIP-1b, KC and IL-33. In some embodiments, the disclosed methods reduce IL-4. In some embodiments, the disclosed methods reduce IL-6. In some embodiments, the disclosed methods reduce IL-17A. In some embodiments, the disclosed methods reduce TNR-α. In some embodiments, the disclosed methods reduce MIP-1b. In some embodiments, the disclosed methods reduce KC. In some embodiments, the disclosed methods reduce IL-33. In some embodiments, the method of decreasing pro-inflammatory cytokines in a patient comprises preventing and/or treating inflammatory diseases, such as, but not limited to, inflammatory bowel disease or colitis.

In some embodiments, the present invention provides a method of reducing IgE in a patient in need thereof, the method comprising administering an effective dose of a compound represented by Chemical Formula 1, or an isomer, pharmaceutically acceptable salt, or a pharmaceutical composition thereof to the patient.

In some embodiments, the present invention provides a method of increasing differentiation of regulatory T cells ($T_{reg}$) in a patient in need thereof, the method comprising administering an effective dose of a compound represented by Chemical Formula 1, or an isomer, pharmaceutically acceptable salt, or a pharmaceutical composition thereof to a patient. In some embodiments, the method of increasing differentiation of regulatory T cells ($T_{reg}$) in a patient comprises preventing and/or treating inflammatory diseases, such as, but not limited to, an autoimmune disease.

In some embodiments, the present invention provides a method of decreasing pro-inflammatory T cells (e.g., Th17) in a patient in need thereof, the method comprising administering an effective dose of a compound represented by Chemical Formula 1, or an isomer, pharmaceutically acceptable salt, or a pharmaceutical composition thereof to a patient. In some embodiments, the method of decreasing pro-inflammatory T cells (e.g., Th 17) in a patient comprises preventing and/or treating inflammatory diseases, such as, but not limited to, an autoimmune disease.

In some embodiments, the present invention provides a method of increasing differentiation of regulatory T cells ($T_{reg}$) and decreasing pro-inflammatory T cells (e.g., Th 17) in a patient in need thereof, the method comprising administering an effective dose of a compound represented by Chemical Formula 1, or an isomer, pharmaceutically acceptable salt, or a pharmaceutical composition thereof to a patient. In some embodiments, the method of increasing differentiation of regulatory T cells ($T_{reg}$) and decreasing pro-inflammatory T cells (e.g., Th17) in a patient comprises preventing and/or treating inflammatory diseases, such as, but not limited to, an autoimmune disease.

In some embodiments the inflammatory disease which can be treated according to the methods of this invention is a Th17-mediated disease, but is not limited to that disease. In some embodiments the Th17-mediated disease is selected from systemic lupus erythematosus, multiple sclerosis, and/or an inflammatory bowel disease, such as, but not limited to, Crohn's disease or ulcerative colitis.

In some embodiments, the present invention provides a method for preventing and/or treating inflammatory diseases for a patient in need thereof, the method comprising administering an effective dose of a compound represented by Chemical Formula 1, or an isomer, pharmaceutically acceptable salt, or a pharmaceutical composition thereof to the patient.

In some embodiments, a compound of the present invention represented by Chemical Formula 1, or an isomer, pharmaceutically acceptable salt, or a pharmaceutical composition thereof are useful in the prevention and/or treatment of inflammatory or obstructive airway diseases, resulting, for example, but not limited to, in reduction of tissue damage, airway inflammation, bronchial hyperreactivity, remodeling, or disease progression. In some embodiments, obstructive airway diseases include obstructive airway diseases having an inflammatory component. Inflammatory or obstructive airway diseases to which the present invention is applicable include but are not limited to: asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma also is to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics.

In some embodiments, a compound of the present invention represented by Chemical Formula 1, or an isomer, pharmaceutically acceptable salt, or a pharmaceutical composition thereof are useful in the prevention and/or treatment of heteroimmune diseases. Examples of such heteroimmune diseases include, but are not limited to, graft versus host disease, transplantation, transfusion, anaphylaxis, allergies (e.g., allergies to plant pollens, latex, drugs, foods, insect poisons, animal hair, animal dander, dust mites, cockroach calyx, or other sources), type I hypersensitivity, allergic conjunctivitis, allergic rhinitis, and atopic dermatitis.

Prophylactic efficacy in the treatment of asthma will be evidenced for this invention by reduced frequency or severity of symptomatic attack, but not limited to this, e.g., of acute asthmatic or bronchoconstrictor attack, improvement in lung function, and/or improved airway hyperreactivity. Such efficacy may further be evidenced by reduced requirement for other symptomatic therapy, such as, but not limited to, therapy for or intended to restrict or abort symptomatic attack when it occurs, for example anti-inflammatory or bronchodilatory. Prophylactic benefit in asthma may in particular be apparent in subjects prone to "morning dipping". Morning dipping is a recognized asthmatic syndrome, common to a substantial percentage of asthmatics and characterized by asthma attack, e.g., between the hours of about 4 to 6 AM, i.e., at a time normally substantially distant from any previously administered symptomatic asthma therapy.

In some embodiments, a compound of the present invention represented by Chemical Formula 1, or an isomer, pharmaceutically acceptable salt, or a pharmaceutical composition thereof are useful in the prevention and/or treatment of other inflammatory or obstructive airway diseases and conditions to which the present invention is applicable and include but are not limited to acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airway hyperreactivity consequent to other drug therapy, in particular other inhaled drug therapy. The invention also is applicable to the prevention and/or treatment of bronchitis of whatever type or genesis including, but not limited to, acute, arachidic, catarrhal, croupous, chronic, or phthinoid bronchitis. Further inflammatory or obstructive airway diseases to which the present invention is applicable include but are not limited to pneumoconiosis (an inflammatory, commonly occupational, disease of the lungs, frequently accompanied by airway obstruction, whether chronic or acute, and occasioned by repeated inhalation of dusts) of whatever type or genesis, including, for example, aluminosis, anthracosis, asbestosis, chalicosis, ptosis, siderosis, silicosis, tabacosis, and/or byssinosis.

With regard to their anti-inflammatory activity, in particular in relation to inhibition of eosinophil activation, a compound of the present invention represented by Chemical Formula 1, or an isomer, pharmaceutically acceptable salt, or a pharmaceutical composition thereof are also useful in the prevention and/or treatment of eosinophil-related disorders, e.g. eosinophilia, in particular eosinophil-related disorders of the airways (e.g., involving morbid eosinophilic infiltration of pulmonary tissues) including but not limited to hypereosinophilia as it affects the airways and/or lungs as well as, for example, eosinophil-related disorders of the airways consequential or concomitant to Loffler's syndrome, eosinophilic pneumonia, parasitic (in particular metazoan) infestation (including tropical eosinophilia). bronchopulmonary aspergillosis, polyarteritis nodosa (including Churg-Strauss syndrome), eosinophilic granuloma, and/or eosinophil-related disorders affecting the airways occasioned by drug reaction.

In some embodiments, a compound of the present invention represented by Chemical Formula 1, or an isomer, pharmaceutically acceptable salt, or a pharmaceutical composition thereof are useful in the prevention and/or treatment of inflammatory or allergic conditions of the skin; for example, but not limited to, psoriasis, contact dermatitis, atopic dermatitis, alopecia areata, erythema multiforme, dermatitis herpetiformis, hidradenitis suppurativa, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita (EBA), acne vulgaris, and/or other inflammatory or allergic conditions of the skin.

In some embodiments, a compound of the present invention represented by Chemical Formula 1. or an isomer, pharmaceutically acceptable salt, or a pharmaceutical composition thereof are useful for the prevention and/or treatment of inflammatory diseases or conditions, including but not limited to diseases or conditions having an inflammatory component; for example, graft versus host disease (GvHD), chronic obstructive airway disease, obstructive pulmonary disease, allergy, systemic lupus erythematosus, scleroderma, inflammatory bowel disease (e.g., ulcerative colitis and Crohn's disease), atopic dermatitis, psoriasis, anaphylaxis, dermatitis, diabetic retinosis, retinitis, macular degeneration, uveitis, conjunctivitis, rheumatoid arthritis, ankylosing spondylitis, osteoarthritis, osteoporosis, diabetes, diabetic kidney disease, nephritis, Sjogren's syndrome, autoimmune pancreatitis, periodontal disease, alopecia arcata, chronic pelvic inflammatory disease, endometriosis, rhinitis, tonsilitis, otitis media, sore throat, cystitis, chronic prostatitis, diseases and conditions of the eye such as ocular allergy, keratoconjunctivitis sicca, vernal conjunctivitis, diseases affecting the nose including allergic rhinitis, and/or inflammatory disease in which autoimmune reactions are implicated or having an autoimmune component or etiology. including but not limited to autoimmune hematological disorders (e.g., hemolytic anemia, aplastic anemia, pure red cell anemia and idiopathic thrombocytopenia), polychondritis, Wegener granulomatosis, dermatomyositis, chronic active hepatitis, myasthenia gravis. Steven-Johnson syndrome, idiopathic sprue, irritable bowel syndrome, celiac disease, periodontitis, hyaline membrane disease, kidney disease, glomerular disease, alcoholic liver disease, multiple sclerosis, endocrine ophthalmopathy, Becker's/Duchenne muscular dystrophy, Grave's disease, sarcoidosis, alveolitis, chronic hypersensitivity pneumonitis, multiple sclerosis, primary biliary cirrhosis, uveitis (anterior and posterior), interstitial lung fibrosis, psoriatic arthritis, systemic juvenile idiopathic arthritis, cryopyrin-associated periodic syndrome, vasculitis, diverticulitis, interstitial cystitis, glomerulonephritis (with and without nephrotic syndrome, e.g. including idiopathic nephrotic syndrome or minimal change nephropathy), chronic granulomatous disease, leptospirosis renal disease, glaucoma, retinal disease, aging, headache, pain, complex regional pain syndrome, cardiac hypertrophy, muscle atrophy, catabolic disorders, obesity, fetal growth retardation, hypercholesterolemia, heart disease, chronic heart failure, mesothelioma, anhidrotic ectodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, diabetes (Type 1 diabetes or Type 2 diabetes), appendicitis, blepharitis, bronchiolitis, bronchitis, bursitis, cervicitis, cholangitis, cholecystitis, chronic graft rejection, colitis, dacryoadenitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, parotitis, pericarditis, peritonitis, pharyngitis, pleuritis, phlebitis, pneumonitis, pneumonia, polymyositis, proctitis, prostatitis, pyelonephritis, salpingitis, sinusitis, stomatitis, synovitis, tendonitis, tonsillitis, ulcerative colitis, vaginitis, vasculitis, and/or vulvitis.

In some embodiments, the inflammatory disease is, but not limited to, asthma, acute lung injury, GvHD Graft versus Host Disease), chronic obstructive pulmonary disease, allergy, systemic lupus erythematosus, scleroderma, inflammatory bowel disease (for example ulcerative colitis and Crohn's disease), atopic dermatitis, psoriasis, anaphylaxis, dermatitis, diabetic retinosis, retinitis, macular degeneration, uveitis, conjunctivitis, rheumatoid arthritis, ankylosing spondylitis, osteoarthritis, osteoporosis, diabetes, diabetic kidney disease, nephritis, Sjogren's syndrome, Crohn's disease, autoimmune pancreatitis, periodontal disease, alopecia areata, graft versus host disease, chronic pelvic inflammatory disease, endometriosis, rhinitis, tonsilitis, otitis media, sore throat, cystitis and chronic prostatitis. In certain embodiments, the inflammatory disease is, but not limited to, inflammatory bowel disease, psoriasis, rheumatoid arthritis and lupus.

In some embodiments, the inflammatory disease which can be prevented and/or treated according to the methods of this invention is but is not limited to a disease of the skin. In some embodiments, the inflammatory disease of the skin is but is not limited to being selected from contact dermatitis, atopic dermatitis, alopecia areata, erythema multiforme, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita (EBA), and/or other inflammatory or allergic conditions of the skin.

In some embodiments, the inflammatory disease which can be prevented and/or treated according to the methods of this invention is but is not limited to being selected from acute and chronic gout, chronic gouty arthritis, psoriasis, psoriatic arthritis, rheumatoid arthritis, juvenile rheumatoid arthritis, systemic juvenile idiopathic arthritis (SJIA), cryopyrin associated periodic syndrome (CAPS), and osteoarthritis.

In some embodiments, the inflammatory disease which can be prevented and/or treated according to the methods of this invention is but is not limited to being selected from Sjogren's syndrome, allergic disorders, osteoarthritis, conditions of the eye such as ocular allergy, conjunctivitis, keratoconjunctivitis sicca and vernal conjunctivitis, and/or diseases affecting the nose, such as allergic rhinitis.

Furthermore, the present invention provides a method for improving, preventing, treating and/or alleviating inflammation occurring on the skin and/or mucous membranes, the method comprising applying, on a patient requiring improvement and/or alleviation of inflammation occurring on the skin and/or mucous membranes, a compound represented by Chemical Formula 1, or an isomer or pharmaceutically acceptable salt thereof, or a pharmaceutical composition comprising the same.

Furthermore, the present invention provides a use of a compound represented by Chemical Formula 1, an isomer thereof, or a pharmaceutically acceptable salt thereof, or a pharmaceutical composition thereof, for use in preventing and/or treating inflammatory diseases. Specifically, the present invention provides a use of a compound represented by Chemical Formula 1, an isomer thereof, a pharmaceutically acceptable salt thereof, or a pharmaceutical composition thereof, for the production of medicaments for use in preventing and/or treating inflammatory diseases.

The pharmaceutical composition of the present invention, by further comprising excipients, disintegrating agents, sweetening agents, lubricants, flavoring agents and the like, may be formulated using ordinary methods into tablets, capsules, powders, granules, suspensions, emulsions, syrups, topicals, or other liquid or semi-liquid or solid formulations. For example, as the pharmaceutical composition of the present invention may act systemically and/or locally, and may be administered to subjects orally or non-orally, that is, through various pathways such as but not limited to pulmonary route administration, intranasal administration, sublingual administration, lingual administration, buccolingual administration, rectal administration, dermal administration, transdermal administration, or conjunctival administration, the pharmaceutical composition may be formulated into a form suitable for the administration pathway. For example, dosage forms suitable for oral administration are but not limited to formulations comprising a compound of the present invention in crystalline and/or amorphous and/or dissolved form, and may be, for example, tablets (coated or non-coated tablets, for example, using gastric fluid-resistant, delayed-dissolution or insoluble coatings), tablets or films/oblates which rapidly disintegrate in the oral cavity, films/freeze-dried preparations, capsules (for example, hard or soft gelatin capsules), sugar-coated tablets, chewables (for example, soft chewables), granules, pellets, powders, emulsions, suspensions, aerosols and/or solutions. Parenteral administration may be achieved by avoiding the absorption stage (for example, through intravenous, intraarterial, intra cardiac, intrathecal or intra lumbar administration) or including absorption (for example, through intramuscular, dermal, intradermal, subdermal, percutaneous or intraperitoneal pathways). Dosage forms suitable for parenteral administration may include but are not limited to solutions, suspensions, emulsions, freeze-dried preparations, or preparations in the form of sterilized powders for injection.

In some embodiments, the present invention provides a method for preventing and/or treating inflammatory diseases for a patient in need thereof, the method comprising conjointly administering an effective dose of a compound represented by Chemical Formula 1, or an isomer, pharmaceutically acceptable salt, or pharmaceutical composition thereof and at least one additional active ingredient.

In some embodiments, the pharmaceutical composition of the present invention may, for more effective treatment and/or prevention of inflammatory disease, comprise, in addition to a compound of the present invention, at least one additional active ingredient. Active ingredients that may be suitable for combination include but are not limited to gamma globulin, immunomodulatory and immunosuppressive compounds (for example, cyclosporine, Methotrexate®), TNF antagonists (for example, Humira®, etanercept, infliximab), IL-1 inhibitors (for example, anakinra, canakinumab, rilonacept), phosphodiesterase inhibitors (for example, apremilast), JAK/STAT inhibitors (for example, tofacitinib, baricitinib, GLPG0634), IRAK4 inhibitors, leflunomide, cyclophosphamide, rituximab, belimumab, tacrolimus, rapamycin, mycophenolate mofetil, interferon, corticosteroids (for example, prednisone, prednisolone, methylprednisolone, hydrocortisone, betamethasone), cyclophosphamide, azathioprine, sulfasalazine, paracetamol, and/or a non-steroidal anti-inflammatory agent (NSAID) (for example, aspirin, ibuprofen, naproxen, etodolac, celecoxib, colchicine).

Additional active agents that may be used in combination with a compound represented by Chemical Formula 1, or an isomer, pharmaceutically acceptable salt, or pharmaceutical composition thereof, may be but are not limited to small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Acrobid®), Afviar®, Symbicort®, Dulera®, cromolyn sodium (Intal®), methylxanthines such as theophylline (Theo-Dur®, Theolair®, Slo-Bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and/or dexamethasone (Decadron®) in combination with lenalidomide (Revlimid®), or any combination(s) thereof.

In another embodiment, the present invention provides a method of preventing and/or treating gout comprising administering to a patient in need thereof a compound of formula I and one or more additional active agents selected from non-steroidal anti-inflammatory drugs (NSAIDS) such as aspirin, ibuprofen, naproxen, ctodolac (Lodine®) and celecoxib, colchicine (Colcrys®), corticosteroids such as prednisone, prednisolone, methylprednisolone, hydrocortisone, and/or the like, probenecid, allopurinol and febuxostat (Uloric®).

In another embodiment, the present invention provides a method of preventing and/or treating rheumatoid arthritis comprising administering to a patient in need thereof a compound of formula I and one or more additional therapeutic agents selected from non-steroidal anti-inflammatory drugs (NSAIDS) such as but not limited to aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and/or "anti-IL-6" agents such as tocilizumab (Actemra®).

In some embodiments, the present invention provides a method of preventing and/or treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®), and/or monoclonal antibodies such as tanczumab.

In some embodiments, the present invention provides a method of preventing and/or treating lupus comprising administering to a patient in need thereof a compound of formula I and one or more additional therapeutic agents selected from acetaminophen, non-steroidal anti-inflammatory drugs (NSAIDS) such as aspirin, ibuprofen, naproxen, ctodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and/or anticoagulants such as heparin (Calcinparine® or Liquacmin®) and warfarin (Coumadin®).

In some embodiments, the present invention provides a method of preventing and/or treating inflammatory bowel disease comprising administering to a patient in need thereof a compound of formula I and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and/or antibiotics such as Flagyl or ciprofloxacin.

In some embodiments, the present invention provides a method of preventing and/or treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®), Slo-Bid®, Uniphyl®, Theo-24®) and aminophylline, and/or IgE antibodies such as omalizumab (Xolair®).

In some embodiments, the present invention provides a method of preventing and/or treating COPD comprising administering to a patient in need thereof a compound of formula I and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®), Slo-Bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and/or Dulera®.

Addition embodiments of the present invention are described below. These embodiments are illustrative and should not be construed as limiting the scope of the claimed invention.

Embodiment 1. A pharmaceutical composition for preventing and/or treating inflammatory diseases, the composition comprising, as an active substance, a compound represented by Chemical Formula 1, or an isomer or pharmaceutically acceptable salt thereof:

[Chemical Formula 1]

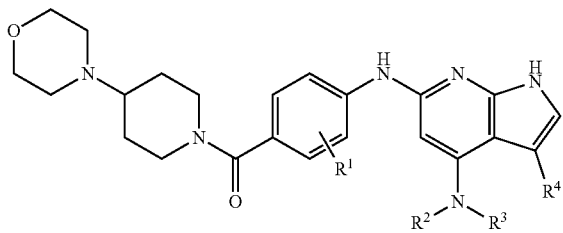

(where, in Chemical Formula 1 above,
$R^1$ is $C_1$-$C_3$ alkoxy;
$R^2$ and $R^3$ are each independently hydrogen, straight chain or branched chain $C_1$-$C_{10}$ alkyl, or $C_3$-$C_6$ cycloalkyl; and
$R^4$ is haloalkyl).

Embodiment 2. The pharmaceutical composition for preventing and/or treating inflammatory disease of embodiment 1, the composition comprising, as an active substance, a compound wherein, $R^1$ is methoxy; $R^2$ is straight chain or branched chain $C_1$-$C_5$ alkyl, or $C_3$-$C_4$ cycloalkyl; $R^3$ is hydrogen; and $R^4$ may be trifluoromethyl, or an isomer or pharmaceutically acceptable salt thereof.

Embodiment 3. The pharmaceutical composition for preventing and/or treating inflammatory disease of embodiment 1, the composition comprising, as an active substance, a compound, or an isomer or pharmaceutically acceptable salt thereof, where the compound represented by Chemical Formula 1 may be (4-((-4-ethylamino)-3-(trifluoromethyl)-1H-pyrrolo[2,3-b]pyridine-6-yl)amino)-3-methoxyphenyl)(4-morpholinopiperidine-1-yl) methanone.

Embodiment 4. The pharmaceutical composition for preventing and/or treating inflammatory disease of any one of embodiment 1 through embodiment 3, the composition comprising, as an active substance, a compound, or an isomer or pharmaceutically acceptable salt thereof, where the inflammatory disease is at least one selected from a group comprising asthma, acute lung injury, graft versus host disease (GvHD), chronic obstructive pulmonary disease, allergy, systemic lupus erythematosus, scleroderma, inflammatory bowel disease (for example, ulcerative colitis and Crohn's disease), atopic dermatitis, psoriasis, anaphylaxis, dermatitis, diabetic retinosis, retinitis, macular degeneration, uveitis, conjunctivitis, rheumatoid arthritis, ankylosing spondylitis, osteoarthritis, osteoporosis, diabetes, diabetic kidney disease, nephritis, Sjogren's syndrome, Crohn's disease, autoimmune pancreatitis, periodontal disease, alopecia areata, graft versus host disease, chronic pelvic inflammatory disease, endometriosis, rhinitis, tonsilitis, otitis media, sore throat, cystitis and chronic prostatitis.

Embodiment 5. The pharmaceutical composition for preventing and/or treating inflammatory disease of any one of embodiment 1 through embodiment 3, the composition comprising, as an active substance, a compound, or an isomer or pharmaceutically acceptable salt thereof, where the inflammatory disease is at least one selected from a group comprising inflammatory bowel disease, rheumatoid arthritis, lupus, psoriasis, atopic dermatitis, graft versus host disease (GvHD), acute lung injury, alopecia areata, and osteoarthritis.

Embodiment 6. The pharmaceutical composition for preventing and/or treating inflammatory disease of any one of embodiment 1 through embodiment 3, the composition comprising, as an active substance, a compound, or an isomer or pharmaceutically acceptable salt thereof, which inhibits protein kinase activity.

Embodiment 7. The pharmaceutical composition for preventing and/or treating inflammatory disease of any one of embodiment 1 through embodiment 3, the composition comprising, as an active substance, a compound, or an isomer or pharmaceutically acceptable salt thereof, which inhibits inflammation-related factors.

Hereinafter, the present invention will be described in further detail through examples and experimental examples.

However, the following examples and experimental examples are intended only to exemplify the present invention, and the scope of the present invention is not limited to the following examples and experimental examples.

EXEMPLIFICATION

General Synthetic Methods

The compounds of the present invention were prepared according to the methods described in Korean Registered Patent Gazette No. 10-1896568. Chemical structures, compound names, and $H^1$ NMR data for compounds 1 to 5 are showed in Table 1, below.

TABLE 1

| Cmpd | Compound structure | Compound name | $^1$H NMR; MS(ESI) m/z |
|---|---|---|---|
| 1 | 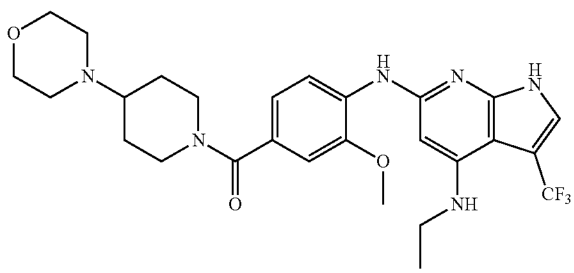 [SMILES: CCNc1cc(Nc2ccc(C(=O)N3CCC(N4CCOCC4)CC3)cc2OC)nc2[nH]cc(C(F)(F)F)c12] | (4-((4-(ethylamino)-3-(trifluoromethyl)-1H-pyrrolo[2,3-b]pyridine-6-yl)amino)-3-methoxyphenyl)(4-morpholinopiperidine-1-yl)methanone | $^1$H NMR (400 MHz, HCl salt, DMSO) δ 11.99 (s, 1H), 11.29 (s, 1H), 9.01 (br s, 1H), 8.20 (br s, 1H), 7.59 (s, 1H), 7.11 (s, 1H), 7.02 (d, J = 8.1 Hz, 1H), 6.12 (s, 1H), 5.41 (br s, 1H), 4.59-3.91 (m, 4H), 3.89 (s, 3H), 3.87-3.80 (m, 2H), 3.38-3.19 (m, 5H), 3.15-2.79 (m, 4H), 2.25-2.12 (m, 2H), 1.76-1.66 (m, 2H), 1.25 (d, J) = 7.1 Hz, 3H); 547 [M + H]$^+$ |

TABLE 1-continued

| Cmpd | Compound structure | Compound name | $^1$H NMR; MS(ESI) m/z |
|---|---|---|---|
| 2 | 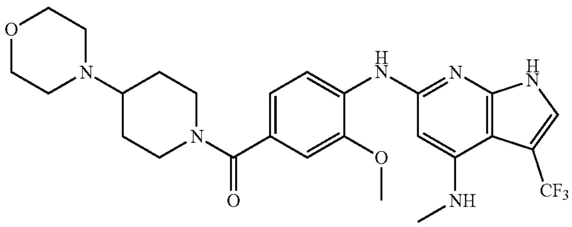 [SMILES: CNc1cc(Nc2ccc(C(=O)N3CCC(N4CCOCC4)CC3)cc2OC)nc2[nH]cc(C(F)(F)F)c12] | (3-methoxy-4-((4-(methylamino)-3-(trifluoromethyl)-1H-pyrrolo[2,3-b]pyridine-6-yl)amino)phenyl)(4-morpholinopiperidine-1-yl)methanone | $^1$H NMR (400 MHz, TFA salt, Methanol-d$_4$) δ 7.55 7.46 (m, 2H), 7.23 (d, J = 1.4 Hz, 1H), 7.13 (dd, J = 8.0, 1.5 Hz, 1H), 5.94 (s, 1H), 4.17 4.00 (m, 2H), 3.93 (s, 3H), 3.87 3.75 (m, 2H), 3.63 3.44 (m, 4H), 3.30 3.15 (m, 4H), 3.04 (s, 3H) 3.02 2.85 (m, 1H), 2.36 2.13 (m, 2H), 1.85 1.70 (m, 2H); 533 [M + H]$^+$ |
| 3 | 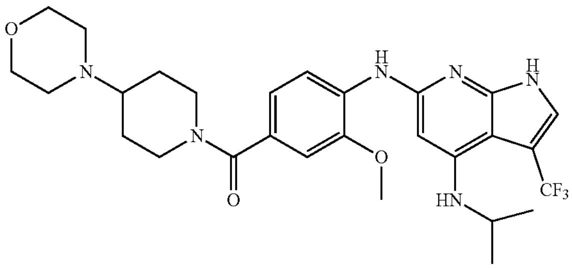 [SMILES: COc1cc(C(=O)N2CCC(N3CCOCC3)CC2)ccc1Nc1cc(NC(C)C)c2c(C(F)(F)F)c[nH]c2n1] | (4-(4-(isopropylamino)-3-(trifluoromethyl)-1H-pyrrolo[2,3-b]pyridine-6-ylamino)-3-methoxyphenyl)(4-morpholinopiperidine-1-yl)methanone | $^1$H NMR (400 MHz, TFA salt, MeOD-d$_4$) δ 7.54-7.52 (m, 2H), 7.23 (s, 1H), 7.14 (d, J = 8.04 Hz, 1H), 5.98 (s, 1H), 4.09-3.98 (m, 3H), 3.93 (s, 3H), 3.89-3.84 (m, 3H), 3.55-3.40 (m, 4H), 3.33-3.13 (m, 4H), 2.24-2.15 (m, 2H), 1.77-1.74 (m, 2H), 1.35 (d, J = 6.28 Hz, 6H); 561[M + H]$^+$ |
| 4 | 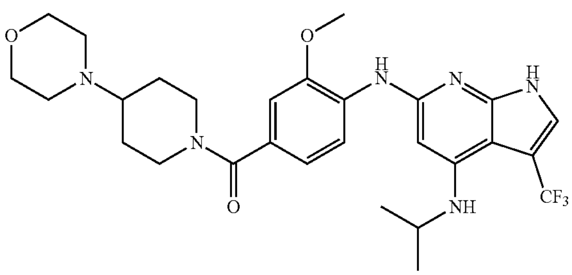 | (S)-(4-((4-(2-butylamino)-3-(trifluoromethyl)-1H-pyrrolo[2,3-b]pyridin-6-yl)amino)-3-methoxyphenyl)(4-morpholinopiperidine-1-yl)methanone | 1H NMR (400 MHz, TFA salt, MeOD) δ 7.41 (s, 1H), 7.40 (d, J = 8.0 Hz, 1H), 7.12 (s, 1H), 6.75 (d, J = 8.0 Hz, 1H), 5.86 (s, 1H), 4.08-3.96 (m, 2H), 3.82 (s, 3H), 3.79-3.51 (m, 3H), 3.49-3.35 (m, 3H), 3.29-3.04 (m, 4H), 2.25-2.04 (m, 2H), 1.84-1.63 (m, 4H), 1.27-1.18 (m, 4H), 0.96-0.84 (m, 4H); 575[M + H]$^+$ |
| 5 | 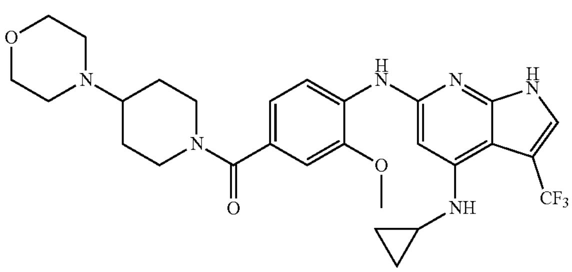 [SMILES: COc1cc(C(=O)N2CCC(N3CCOCC3)CC2)ccc1Nc1cc(NC2CC2)c2c(C(F)(F)F)c[nH]c2n1] | (4-((4-(cyclopropylamino)-3-(trifluoromethyl)-1-((2-(trimethylsilyl)ethoxy)methyl)-1H-pyrrolo[2,3-b]pyridine-6-yl) 3-methoxyphenyl) (4-morpholinopiperidine-1-yl)methanone | $^1$H NMR (400 MHz, TFA salt, MeOD-d$_4$) δ 7.62 (d, J = 8.18 Hz, 1H), 7.50 (s, 1H), 7.24 (s, 1H), 7.15 (d, J = 7.27 Hz), 1H), 6.42 (s, 1H), 4.10-3.99 (m, 2H), 3.98-3.94 (m, 1H), 3.94 (s, 3H), 3.93-3.79 (m, 2H), 3.72-3.49 (m, 3H), 3.34-3.13 (m, 5H), 2.70-2.65 (m, 1H), 2.40-2.14 (m, 2H), 1.85-1.60 (m, 2H), 1.00-0.94 (m, 2H), 0.76-0.68 (m, 2H); 559[M + H]$^+$ |

Example 1. Evaluation of Inhibitory Activity of the Compounds According to the Present Invention on Various Kinases Measuring the enzyme (kinase) selectivity and inhibitory activity of Compound 1 selected from among the example compound of the present invention was consigned to DiscoverX, and a scanMAX™ Kinase analysis panel was used to carry out the experiment. Here, the concentration of the drug used to treat the enzyme was 1 µM in DMSO; the percentage control (% control) was determined using the following method, and the results are shown in Table 2.

[(Example compound−positive control)/(negative control−positive control)×100]

Here, the positive control refers to a compound showing a percentage control of 0%, and the negative control indicates a percentage control of 100% with DMSO. Furthermore, regarding the enzyme selectivity of the present invention, if the percentage control for each enzyme was <41% (that is, less than 41%), the compound was judged to have activity with regard to such enzyme.

TABLE 2

| Item | Protein kinase | Item | Protein kinase |
|---|---|---|---|
| Protein kinases exhibiting inhibition of 59% or more | ALKALK(C1156Y) | Protein kinases exhibiting inhibition of at least 40% and up to 59% | ABL1-nonphosphorylated |
| | ALK(L1196M) | | CAMK2D |
| | CLK1 | | CAMKK2 |
| | CLK2 | | CHEK2 |
| | CLK3 | | CSNK1A1 |
| | CLK4 | | CSNK1E |
| | CSNK1D | | ERK5 |
| | DYRK1A | | HUNK |
| | DYRK1B | | INSR |
| | DYRK2 | | JAK1(JH2domain-pseudokinase) |
| | GAK | | |
| | JNK1 | | JNK2 |
| | LRRK2(G2019S) | | JNK3 |
| | LTK | | LRRK2 |
| | MYLK | | |

TABLE 2-continued

| Item | Protein kinase | Item | Protein kinase |
|---|---|---|---|
| | PAK2 | | MAPKAPK2 |
| | PHKG1 | | PLK4 |
| | PHKG2 | | STK39 |
| | STK33 | | |

As shown in Table 2 above, Compound 1 exhibits inhibitory activity against various protein kinases.

Example 2. Evaluation of Pro-Inflammatory Cytokine Inhibitory Activity of the Compounds According to the Present Invention THP-1 cells were pre-treated with Compound 1 for 1 hour, and then treated with lipopolysaccharides (Lipopolysaccharides, LPS, 0.5 μg/ml), an inflammatory substance, for 24 hours to confirm the expression of the pro-inflammatory cytokines TNF-α and IL-6 by the THP-1 cells and the NF-κb signaling pathway associated with their expression.

Figure 1B:
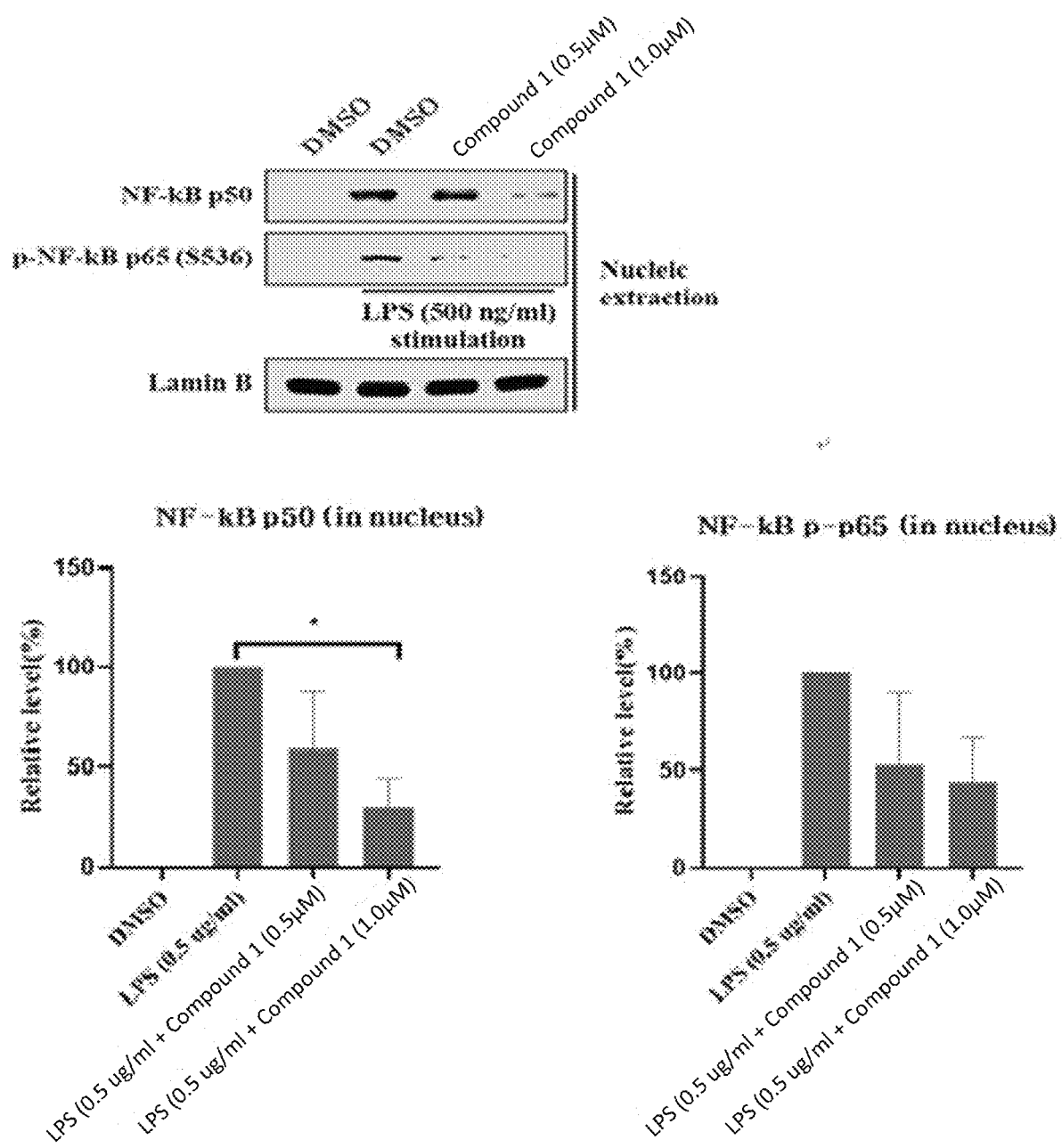

When the THP-1 cells were treated with LPS, the expression of the inflammation-inducing pro-inflammatory cytokines TNF-α and IL-6 increased, and their expression was effectively inhibited by treatment with Compound 1 (FIG. 1a); the expression of such pro-inflammatory cytokines is increased through activation of the NF-κb signaling pathway, and it can be seen that intranuclear movement of p50 and p65, which are associated with the NF-κb signaling pathway, is effectively inhibited by Compound 1 (FIG. 1b). These results confirm that expression of pro-inflammatory cytokines by immune cells is effectively inhibited by Compound 1, and can be interpreted as demonstrating potential for use of Compound 1 in treatment of inflammatory diseases.

Example 3. Evaluation of the Regulation Activity of the Compounds According to the Present Invention Against Regulatory T Cell and Th17 Cell Differentiation Using naive T cells in the mouse spleen, Compound 1 was sufficiently dissolved in DMSO for the differentiation conditions of regulatory T cells and Th17 cells to confirm differentiation. The experiment was conducted using Harmine as a control.

Figure 2:
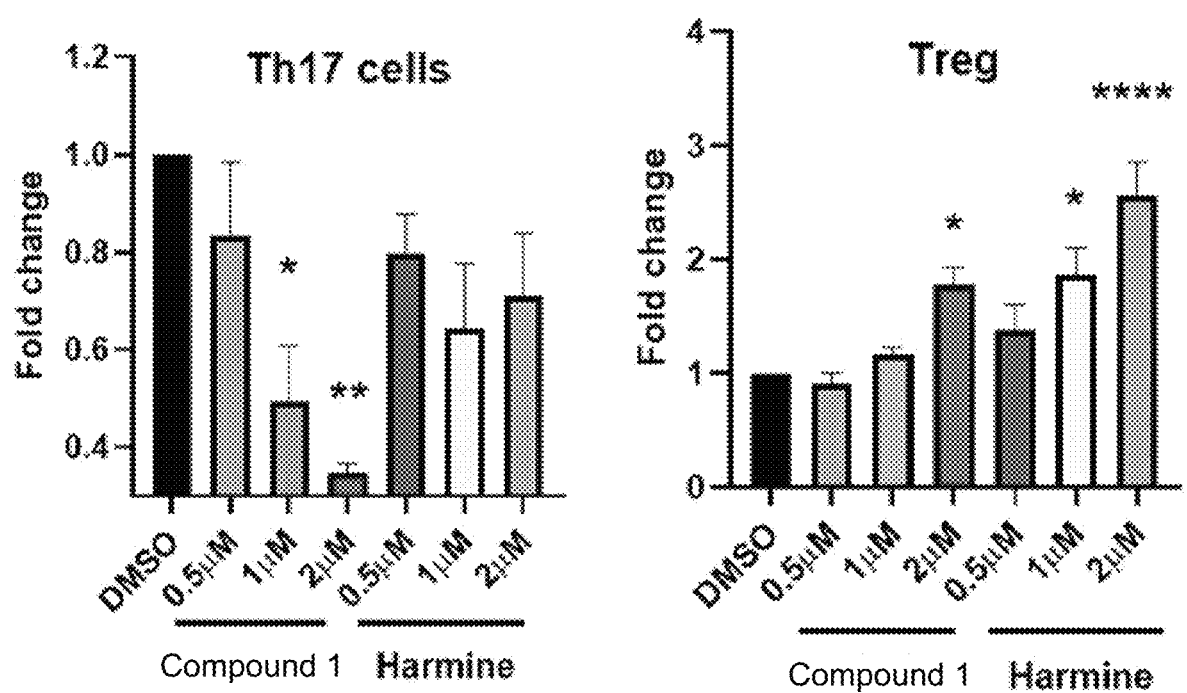
FIG. 2 shows the results of assessing regulation activity against regulatory T cell and Th17 cell differentiation.

In the results, as shown in FIG. 2, when treated with Compound 1, it was found that differentiation of regulatory T cells ($T_{reg}$) increased and differentiation of Th17 cells decreased, indicating potential for use in treatment of inflammatory diseases such as autoimmune disease.

Example 4. Evaluation of the Efficacy of the Compound of the Present Invention Using a Collagen-Induced Arthritis Mouse Model In the present experiment, male DBA-1 mice aged 8 to 10 weeks were used as the animal model. After mixing Bovine Type II Collagen (CII) with the same amount of complete Freud's adjuvant, 100 μL was injected by intradermal injection into the tail of the DBA-1 mouse. After 21 days, the same CII was mixed with the same amount of incomplete Freud's adjuvant (IFA, Chondrex), then 100 μL was injected by intradermal injection into the tail. Observation of symptoms of the mouse model began at this point, and arthritis assessment was carried out every other day. Compound 1 was sufficiently dissolved in a solvent (1% citric acid+20% HP-beta-CD) and then orally administered at 30 mg/kg twice a day for 2 weeks starting on day 29. In the case of the control group Enbrel (anti-TNF-α), 10 mg/kg was subcutaneously administered once every 2 days, then dexamethasone (0.15 mg/kg), Baricitinib (5 mg/kg), Filgotinib (50 mg/kg), and Tofacitinib (10 mg/kg) were orally administered twice a day; as for arthritis assessment, the scores assessed at the four feet of the mouse were added and divided by 4 to give a mean, based on the mean arthritic index by Rosloniec et al (Reference Literature 1: Brand D D, et al. Nat Protoc. 2007:2(5): 1269-75).

The scores and criteria for the arthritis assessment are as follows.

Score 0: No edema or erythema.
Score 1: Mild edema and erythema limited to the foot or ankle joint
Score 2: Mild edema and erythema from the ankle joint to the tarsals
Score 3: Moderate edema and erythema from the ankle joint to the metatarsals.
Score 4: Severe edema and skin flaring from the ankle to the entire leg, or stiffness in the leg Upon termination of the experiment, the weight of the two hind legs of each mouse were measured and added, and these measurements were compared.

Furthermore, for histological examination of the joint area of the control and the experimental group treated with Compound 1, the tissues were dyed with H&E and T-blue and observed under an optical microscope to evaluate the sum of the degree of joint fibrosis due to necrosis and inflammatory cell infiltration (0 to 5), the structure of the cartilage under examination, cell count and distribution, synovial inflammation and hyperplasia (Modified Rankin Scores, 0 to 12) according to the criteria of Table 3 and the results were compared (Reference 2: Cynthia Shackelford, et al. Toxicologic Pathology. Vol. 30, No. I, p93-96.; Reference 3: Pine P R, et al. Clin Immunol. 124 (3): 244-57).

TABLE 3

| | Arthritis fibromatous with necrosis | Modified Rankin Scores | | |
|---|---|---|---|---|
| Score | and inflammatory cell infiltration | Structure | Cells | Synovial inflammation and hyperplasia |
| 0 | Normal | Normal | Normal | Normal |
| 1 | Less than 1% | Irregular surface formation | Broad hyperplasia | Normal or minute abnormal growth accompanying mild inflammation |
| 2 | 1-25% | Pannus and irregular surface formation | Replication | Moderate inflammation accompanied by mild trophoblastic growth |
| 3 | 26-50% | Splitting at the changing surface | Hypocellular state (necrosis) | Moderate trophoblastic growth accompanying moderate inflammation |
| 4 | 51-75% | Splitting of the tide mark | | Moderate trophoblastic growth accompanying severe inflammation |

TABLE 3-continued

| Score | Arthritis fibromatous with necrosis and inflammatory cell infiltration | Modified Rankin Scores | | |
|---|---|---|---|---|
| | | Structure | Cells | Synovial inflammation and hyperplasia |
| 5 | 76-100% | Splitting of the cartilage | | |
| 6 | | Complete destruction of cartilage tissue | | |

Figure 3:
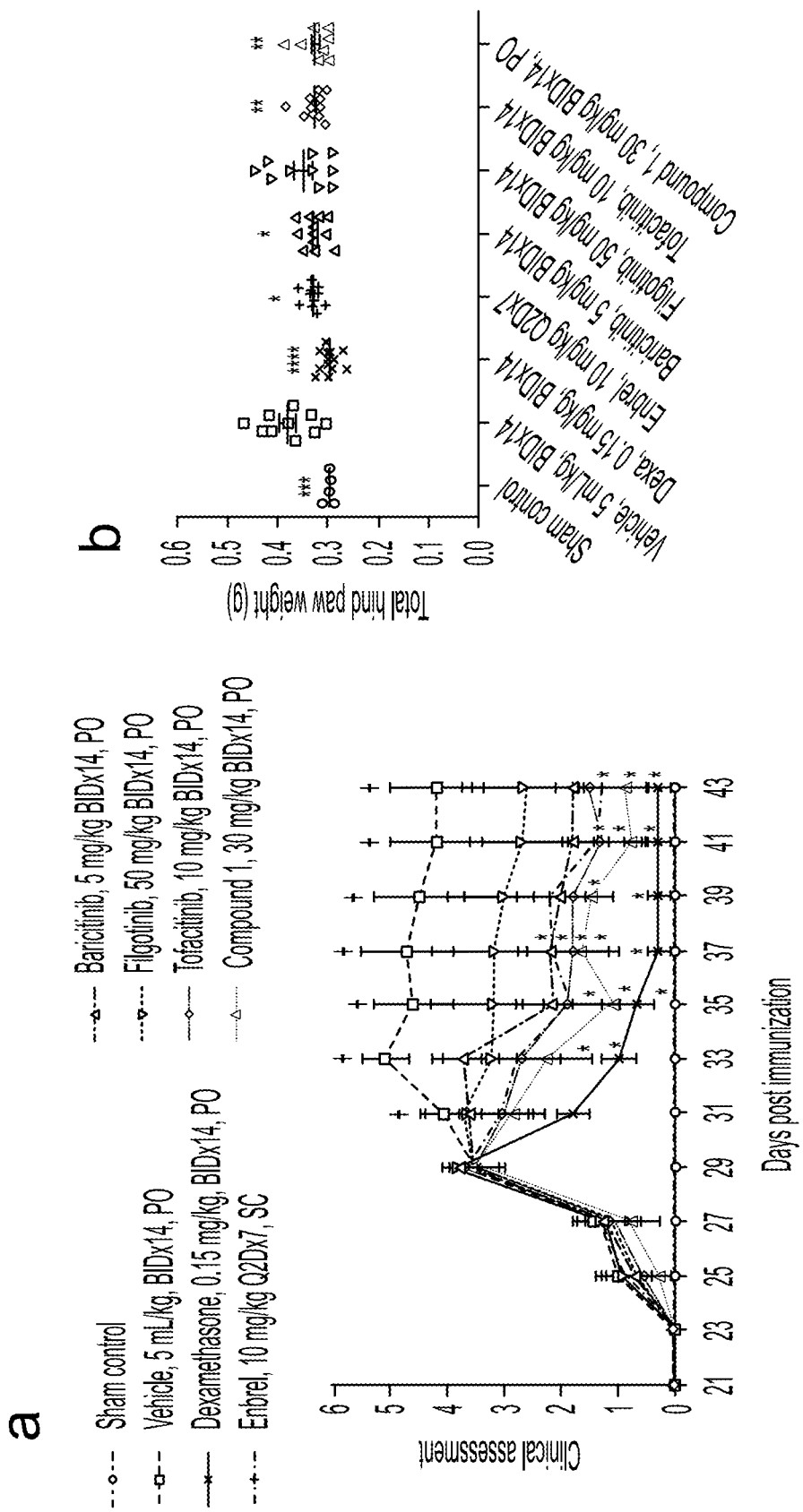
FIG. 3 shows the results of treating a collagen-induced arthritis mouse model with Compound 1 to evaluate the therapeutic effects against arthritis, showing results of arthritis index evaluation (a), joint weight measurement (b), and histologic analysis results (c) through (e) observed under a microscope after dyeing with H&E and T-blue.
Figure 3:
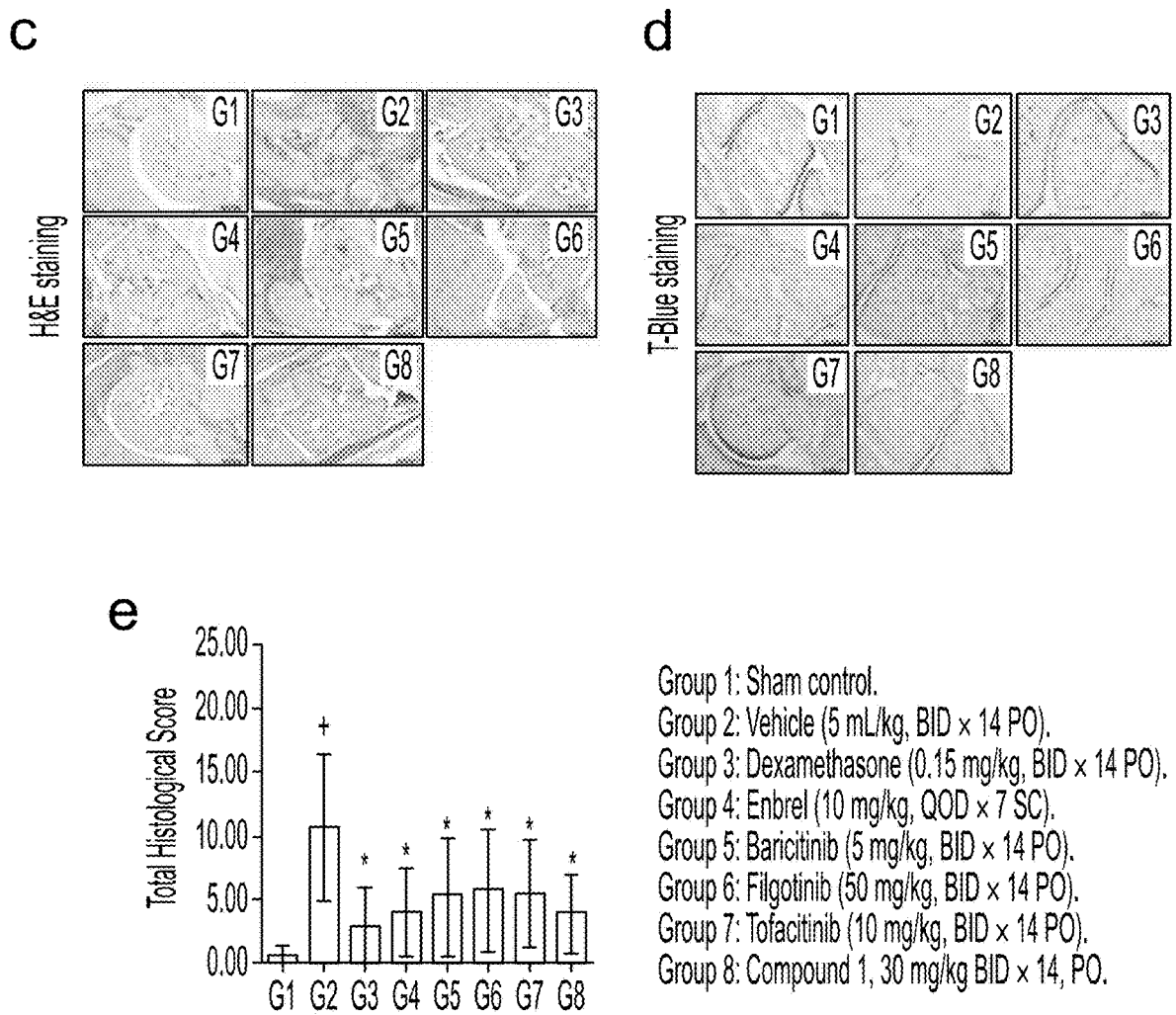

The results of evaluating the arthritis index after inducing inflammation with collagen are shown in FIG. 3. It was determined in the results that the increased arthritic index was reduced when the compound of the present invention was administered, and the weight of the joint, which had increased due to induction of arthritis, was reduced (FIGS. 3a to 3b). Furthermore, based on photography of the joint area for histological analysis, it can be seen that treatment with Compound 1 reduced the area of cells were collagen-induced inflammation had occurred, and also reduced the area of the damaged joint (FIGS. 3c to 3e). This confirms that the above compound inhibits inflammatory reaction and has the potential to treat and suppress the progression of arthritis.

Example 5. Evaluation of Inflammatory Cytokine Expression Inhibition Activity in Peripheral Blood Mononuclear Cells (PBMC) of Inflammatory Bowel Disease Patients Blood was collected from patients with inflammatory bowel disease and the peripheral blood mononuclear cells were isolated within 12 hours of collection; by treating for 24 hours with Compound 1, inflammatory cytokine secretion inhibition activity in peripheral blood mononuclear cells was examined.

Figure 4:
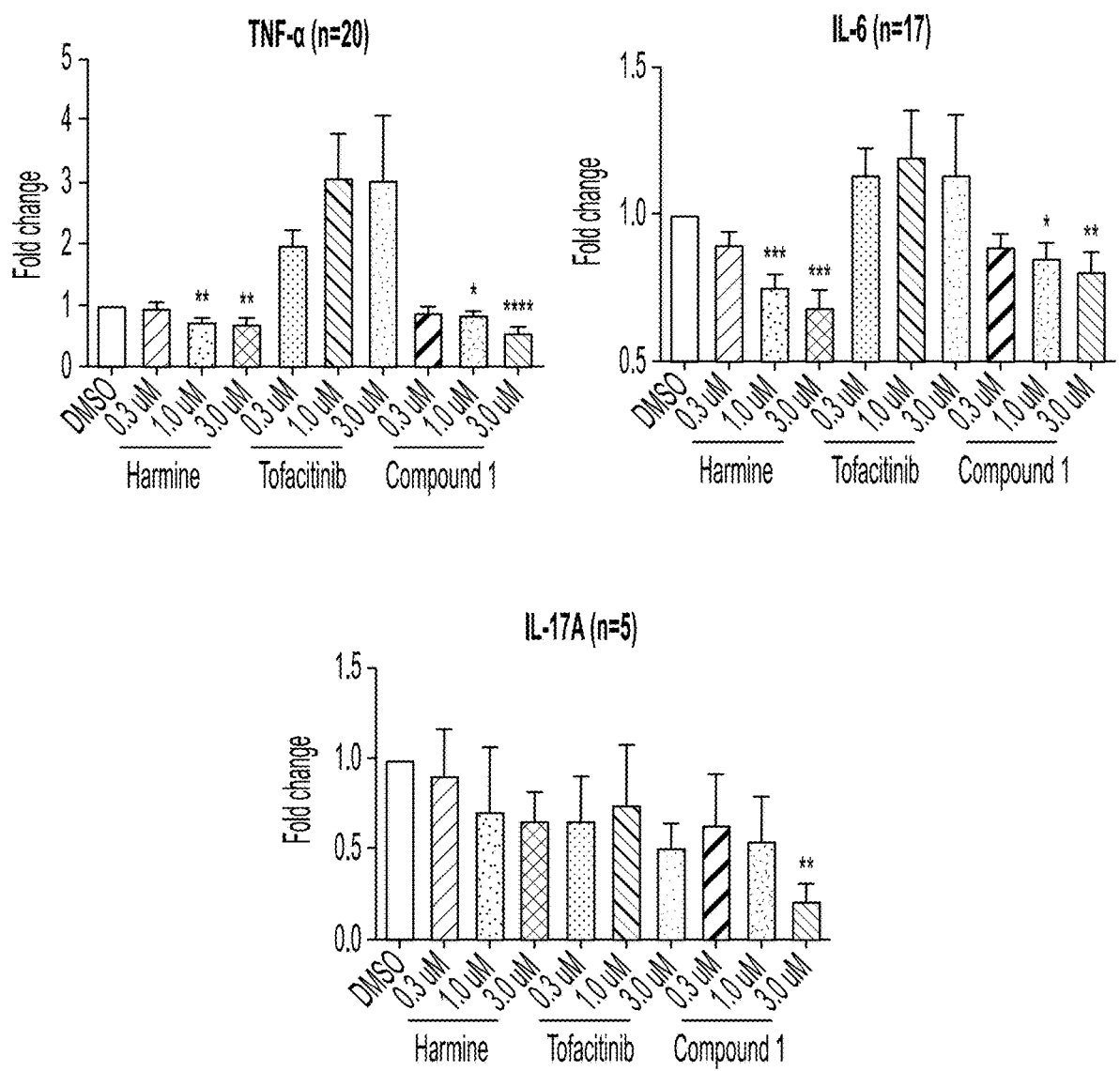
FIG. 4 shows the results of evaluating the inhibitory activity of Compound 1 on the secretion of inflammatory cytokines (TNF-α, IL-6 and IL-17A) when peripheral blood mononuclear cells in the blood of inflammatory bowel disease patients have been treated with various concentrations.

The peripheral blood mononuclear cells of inflammatory bowel disease patients are already activated and express inflammatory cytokines. It was confirmed by treating the peripheral blood mononuclear cells of patients with inflammatory bowel disease with Compound 1 effectively inhibiting expression of the inflammatory cytokines TNF-α, IL-6 and IL-17A, and this result can be interpreted as indicating potential of the compound for use in treatment of inflammatory bowel disease (FIG. 4).

Example 6. Evaluation of the Efficacy of Compounds Using a 2,4,6-Trinitrobenzenesulfonic Acid (TNBS) Induced Colitis Mouse Model In the present experiment, male BALB/c mice (8 weeks old) were used. The experimental animals were subjected to dietary restriction for one day prior to treating with TNBS. Bowel inflammation was induced by administering TNBS (TNBS solution, 1 mg in 0.1 mL 50% ethanol) by submucosal injection in the colon. For the control animals in which inflammation was not induced, only 0.9% NaCl solution without TNBS was administered by submucosal injection in the colon.

Compound 1 was sufficiently dissolved in a solvent (5% DMSO, 5% PEG400, 90% DDW within 1% Tween 80) and then orally administered once daily at the prescribed concentration (60 mpk). The comparative compound, cyclosporine A, was orally administered once daily, and the TNF-α blocker (Enbrel®) was administered intraperitoneally once daily.

During the test, changes in body weight, occult bleeding in stool, and stool consistently were examined every day, and serum was collected on day 5 of the experiment. Bowel tissue was collected at the termination of the experiment to measure the weight of the bowel tissue, degree of polymorphonuclear leukocyte (PMN) deposition and degree of myeloperoxidase (MPO) expression.

Figure 5:
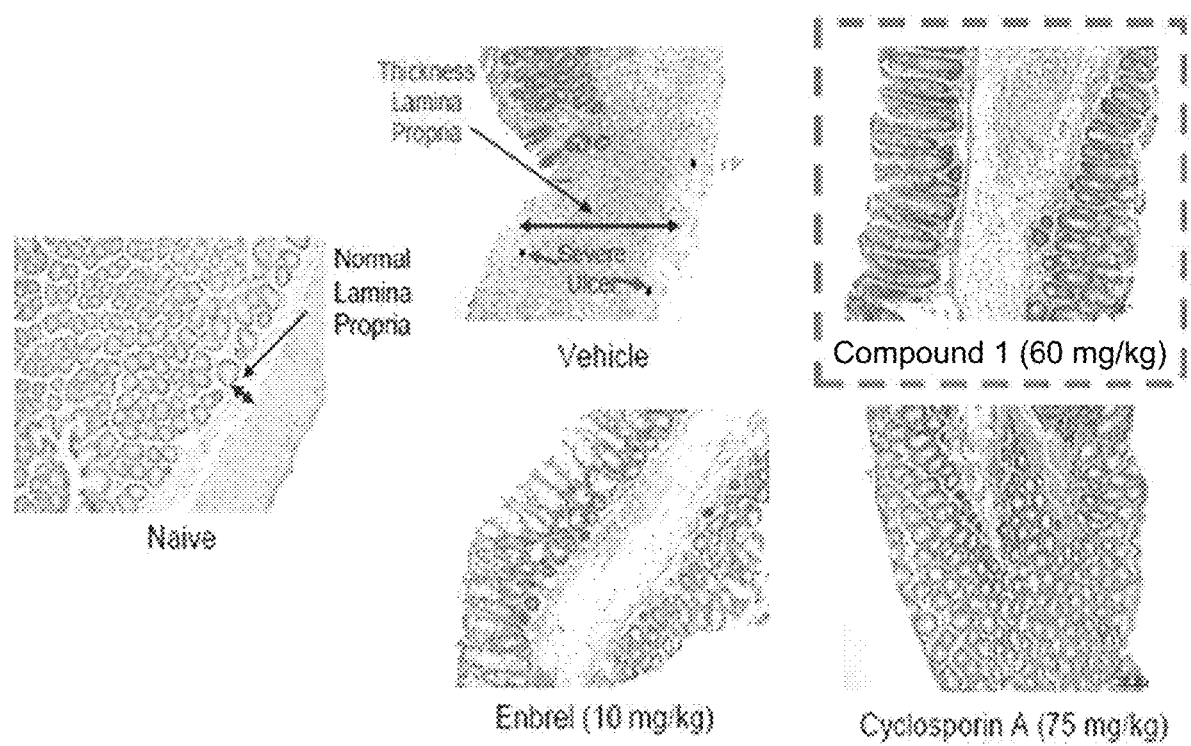
FIG. 5 is a drawing of the result of optical microscope observation after H/E dyeing the colon tissue of a TNBS-induced inflammatory bowel disease mouse model treated with Compound 1 and Enbrel and Cyclosporin A as comparative compounds.
Figure 6:
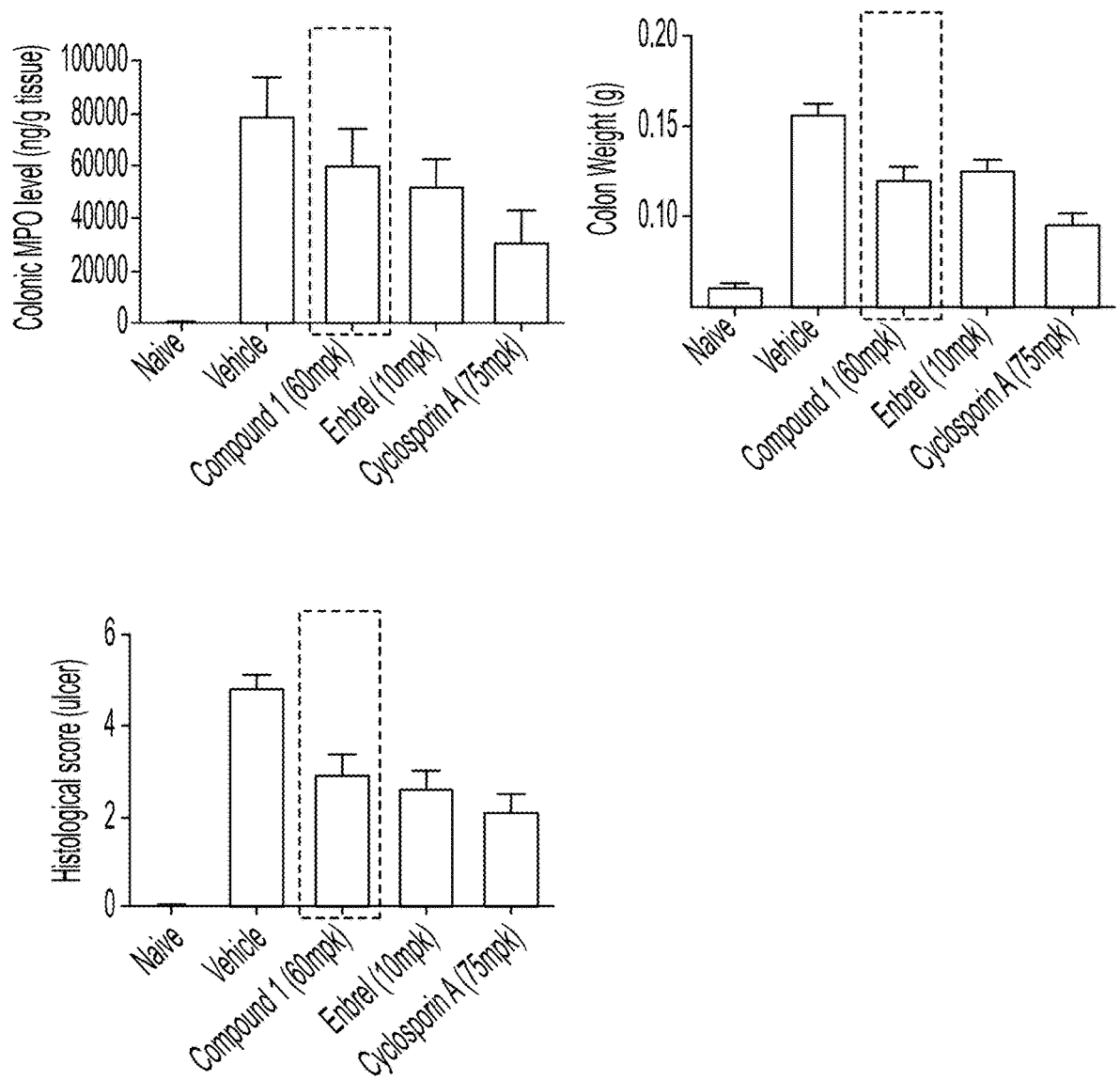
FIG. 6 shows the degree of expression of myeloperoxidase (MPO), as well as the weight and histological analysis results of colon tissue after treatment of a 2,4,6-trinitrobenzenesulfonic acid (TNBS) induced colitis model with Compound 1.

In the results, as shown in FIG. 6, MPO levels were lower than the MPO levels of the control not treated with the compound. Furthermore, weighing the bowel tissue showed a weight reduction in the experimental group treated with Compound 1, and this can be interpreted as being due to the reduction of the edema, etc. caused by inflammation. Additionally, the inflammation sites on the collected bowel tissue were dyed with H&E and photographed with an optical microscope, and the results showed that the lamina propria, whose thickness had increased due to induction of inflammation, decreased in thickness due to treatment with the compound of the present invention (FIG. 5).

Example 7. Evaluation of the Efficacy of the Compounds Using a DSS-Induced Inflammatory Bowel Disease Mouse Model The animals used for the present experiment was male C57BL/6 mice (aged 6 to 8 weeks) weighting 20 to 24 g, purchased from Charles River Laboratories. All the mice except the normal control were made to drink 3% DSS water for 5 days to induce enteritis.

Starting the day after induction of enteritis began, Compound 1 was sufficiently dissolved in solvent (0.5% citric acid in $dH_2O$) then orally administered twice a day at a prescribed concentration (20 mg/kg). The comparative compound cyclosporine A was dissolved in 0.5% methylcellulose solvent and orally administered once a day at a prescribed concentration (20 mg/kg), and Tofacitinib was dissolved in 0.5% methylcellulose solvent and orally administered twice a day at a prescribed concentration (10 mg/kg).

Changes in body weight, occult bleeding in stool, and stool consistently were examined daily during the experiment to assess the degree of disease activity, and upon termination of the experiment (day 12), bowel tissue was collected in order to measure bowel tissue weight and length, perform histological analysis using H&E dyeing and PAS dyeing, and analyze expression of inflammatory cytokines in the bowel tissue.

To assess disease activity, changes in weight and other criteria disclosed in Table 4 below were used for scoring; scores were aggregated.

TABLE 4

| Score | Weight loss | Stool consistency | Occult blood test | Activity |
|---|---|---|---|---|
| 0 | 0.0-4.99% | Normal | None | Active |
| 1 | 5.0-9.99% | | | |
| 2 | 10.0-14.99% | Slightly watery stool | Urinary occult blood and slightly fecal | Obtusion |

TABLE 4-continued

| Score | Weight loss | Stool consistency | Occult blood test | Activity |
|---|---|---|---|---|
| 3 | 15.0-19.99% | | occult blood | |
| 4 | >20.0% | Diarrhea | Severe fecal occult blood | No movement without stimulation |
| 5 | >30.0% | | | Dying |

Figure 7:
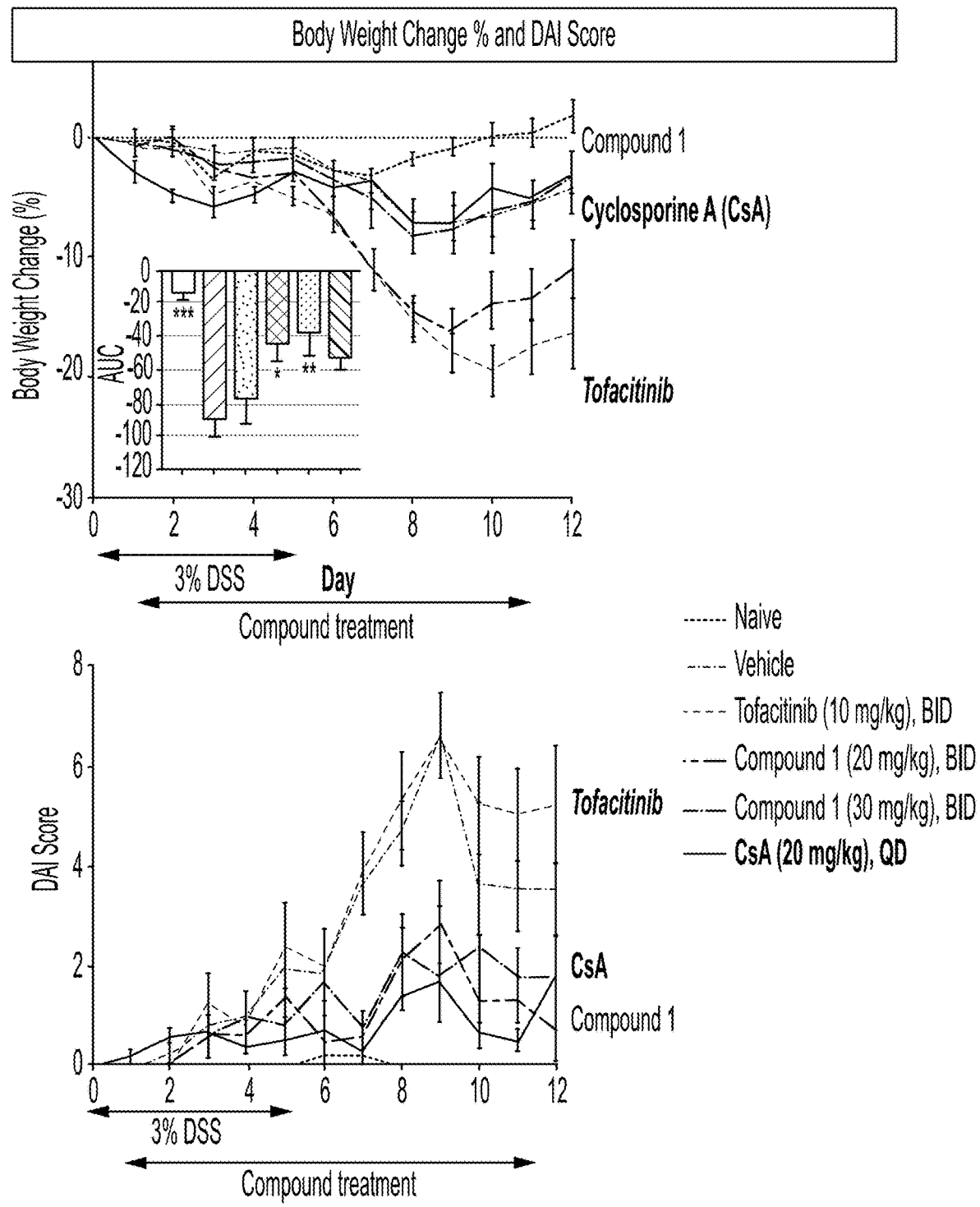
FIG. 7 shows the results of evaluating the efficacy after treating a DSS (dextran sodium sulfate)-induced inflammatory bowel disease mouse model, showing the results of evaluation weight loss suppression effect and disease activity index (DAI).
Figure 8A:
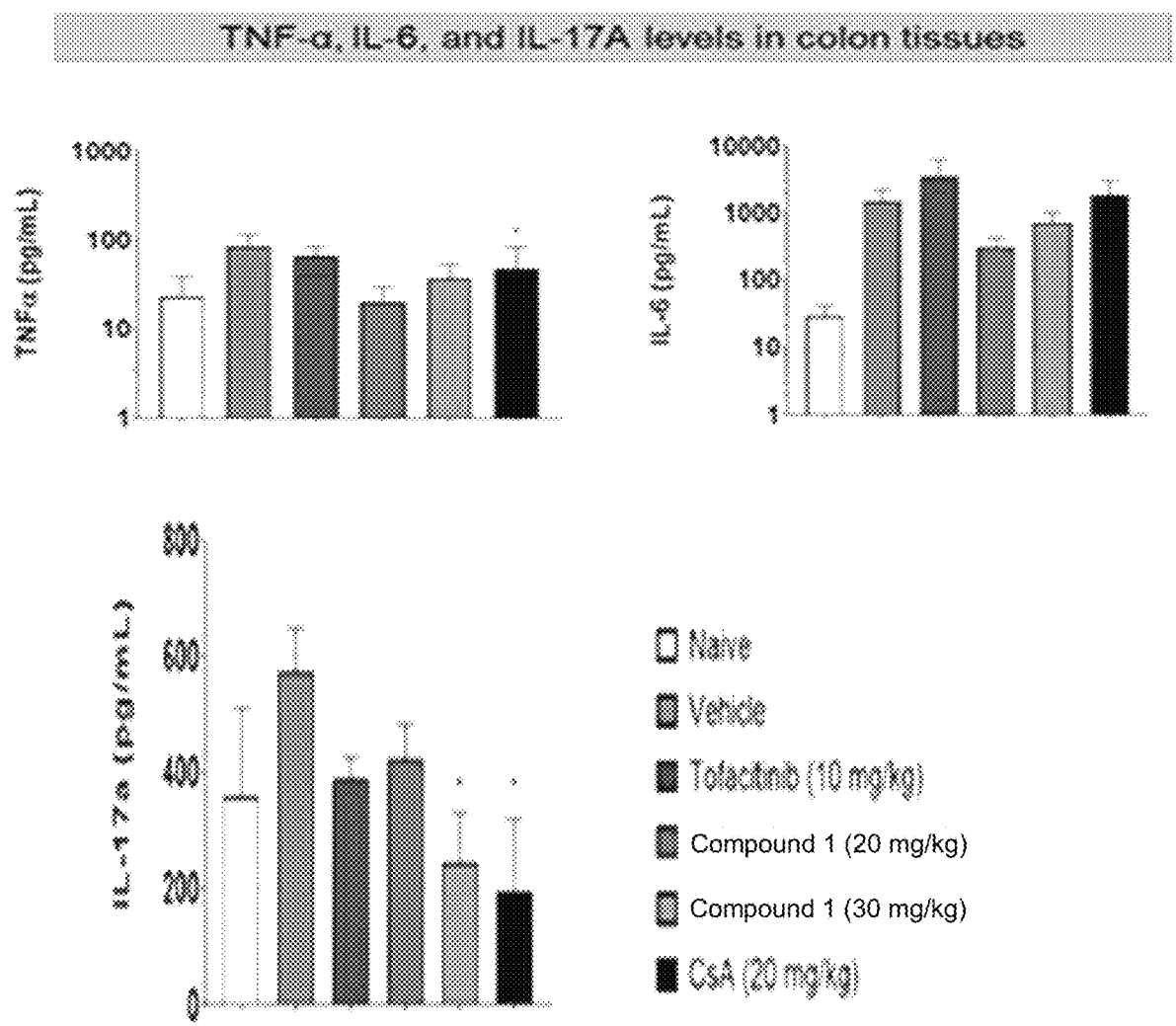
FIG. 8a through FIG. 8c show the expression of inflammatory cytokines in colon tissue of a DSS-induced inflammatory bowel disease mouse model treated with Compound 1 and comparative compounds Cyclosporin A and Tofacitinib (FIG. 8a), an optical microscope photograph of colon tissue after H/E dyeing (FIG. 8b), and the results of scoring the weight to length ratio and Goblet cell depletion of colon tissue (FIG. 8c).
Figure 8B:
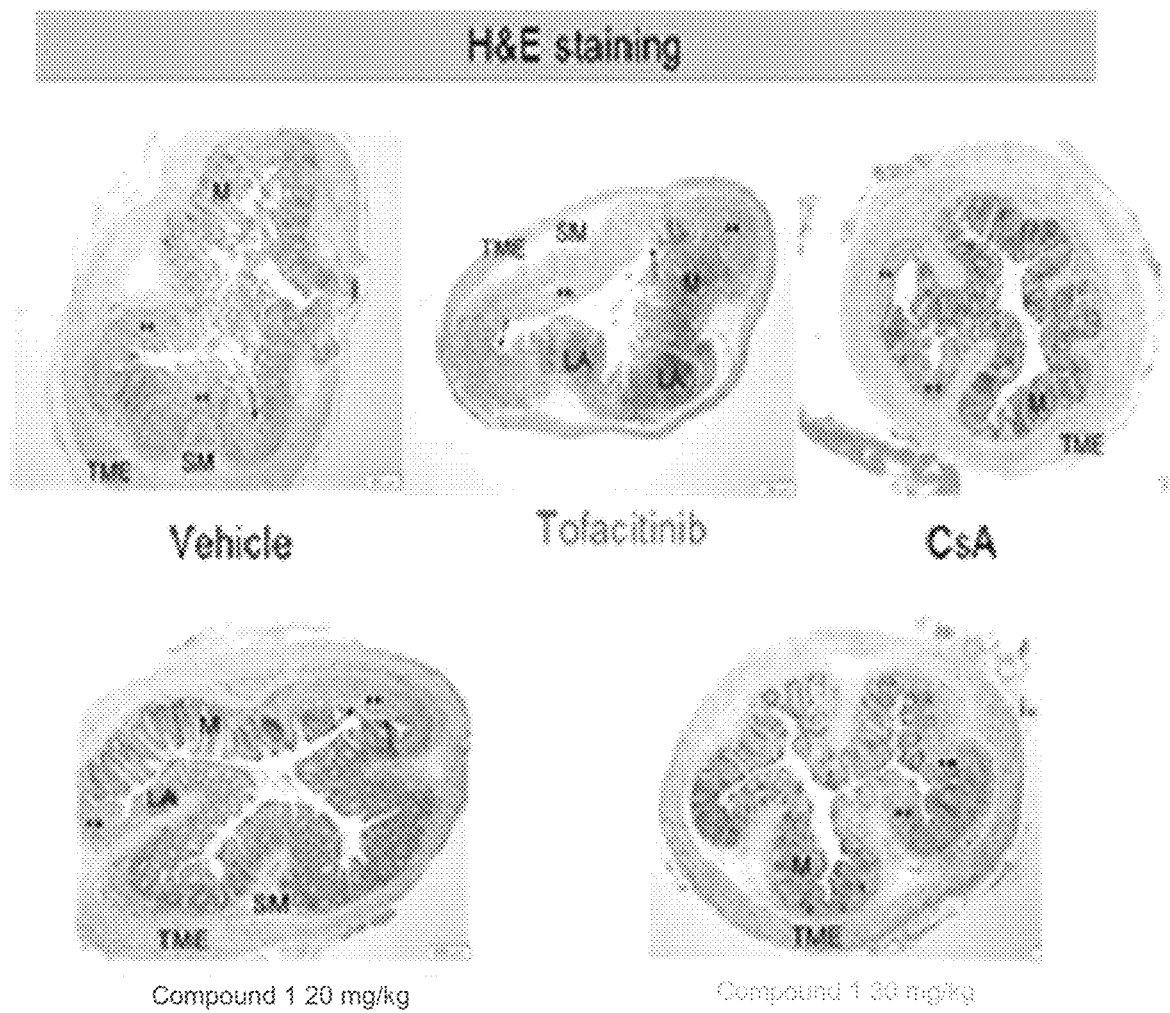
Figure 8C:
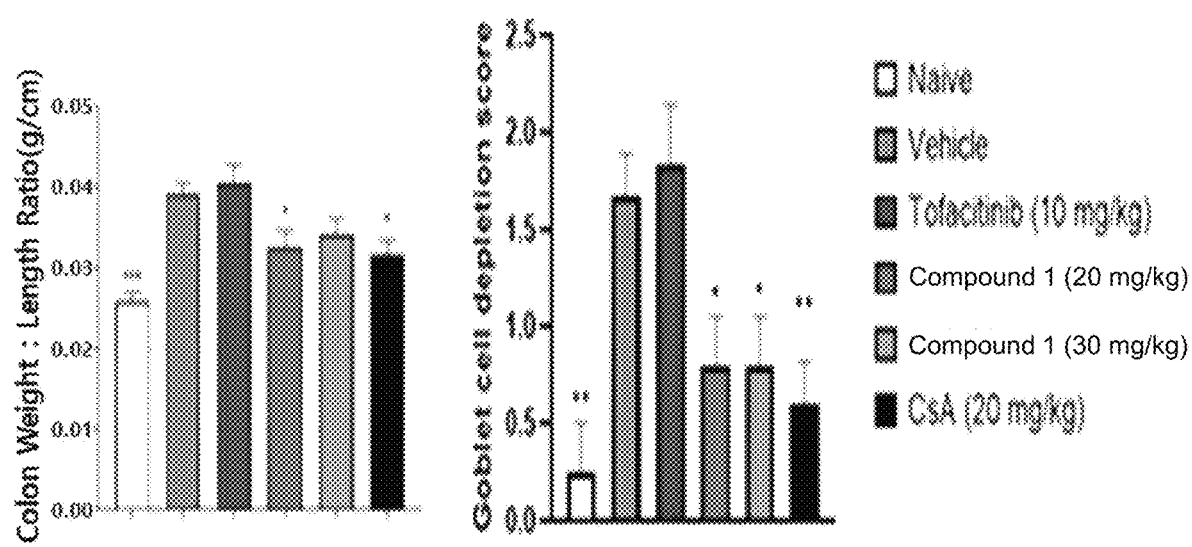

In the results, as shown in FIG. 7, treatment with the compound showed less weight reduction compared to the control group not treated with the compound, and disease activity was reduced to the level of the control administered cyclosporine A. Furthermore, as shown in FIG. 8, whereas the length to weight ratio of bowel tissue increases as colitis becomes more severe, administration of Compound 1 reduced the bowel tissue length to weight ratio, and histological analysis confirmed that loss of goblet cells was also reduced. Additionally, it was confirmed that administration of Compound 1 decreased the expression of inflammatory cytokines (TNR-α, IL-6, IL-17A), which increases as inflammation in bowel tissue is aggravated. In summation, as Compound 1 was confirmed to reduce symptoms caused by colitis (diarrhea, fecal occult bleeding, and inflammatory markers), the results can be interpreted to confirm its potential for use in treating colitis.

Example 8. Evaluation of the Efficacy of the Compounds Using a House Dust Mite-Induced Atopic Dermatitis Model The backs and ears of NC/Nga mice aged 8 weeks were shaved, and 0.1 g house dust mite cream was applied once every three days for a total of seven times to induce atopic dermatitis. For the negative control group where dermatitis was not induced, a cream not including house dust mites was applied. After inducing atopic dermatitis, Compound 1 was sufficiently dissolved in solvent (0.5% citric acid), then orally administered twice daily for 14 days at prescribed concentrations, respectively 10, 20 and 30 mpk. To the comparative control group, the JAK1 inhibitor upadacitinib was orally administered at 6 mg/kg twice daily for 14 days.

Figure 9:
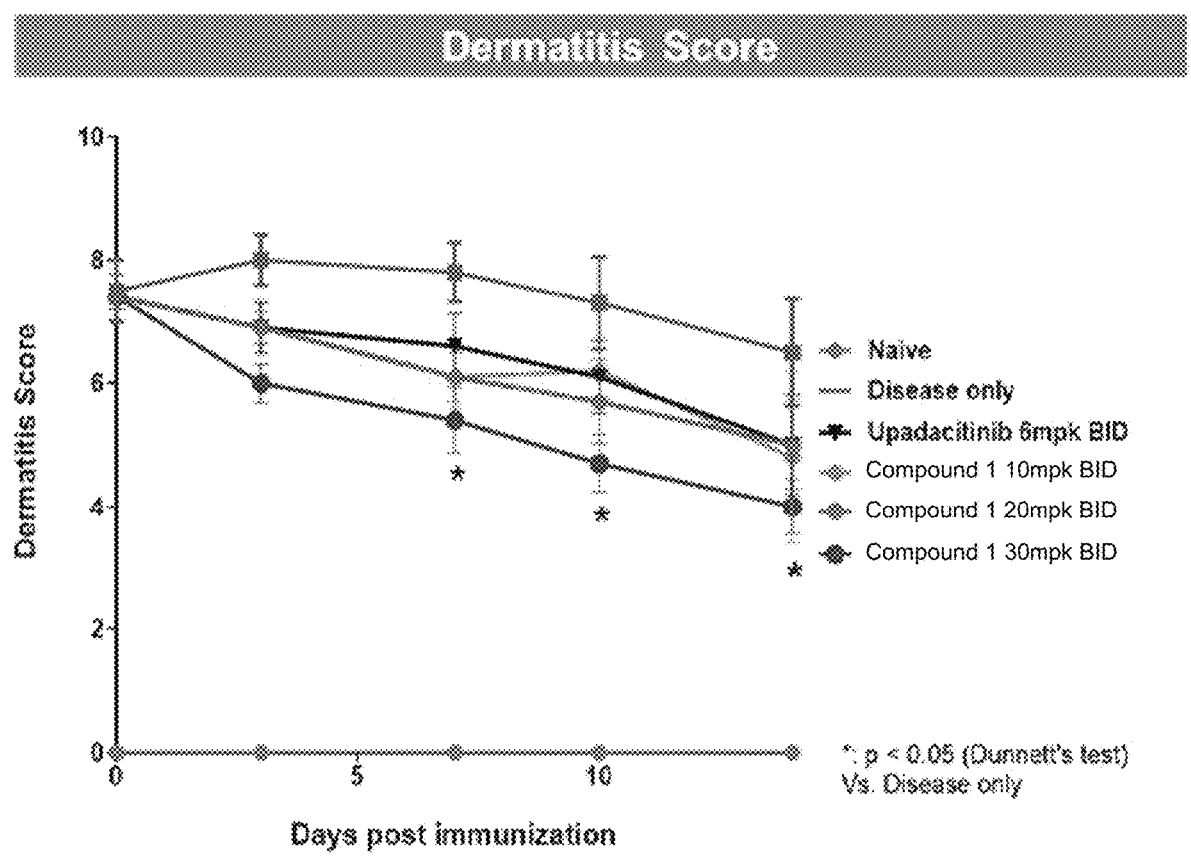
FIG. 9 shows the results of scoring the skin state of a house dust mite-induced atopic dermatitis model to analyze the therapeutic effects of treating a house dust mite-induced atopic dermatitis model with Compound 1.
Figure 10:
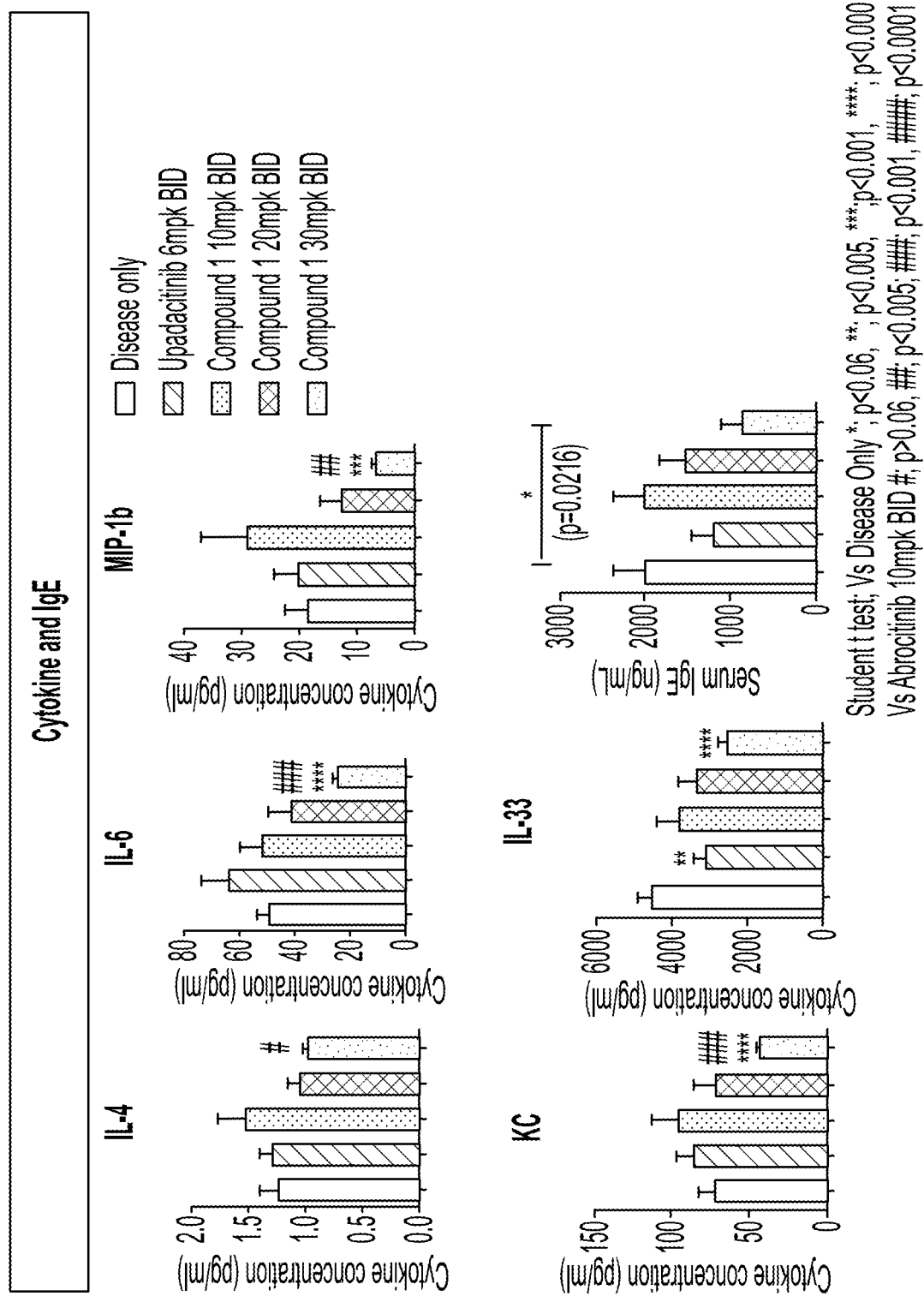
FIG. 10 shows the results of evaluating the inhibitory activity of Compound 1 of IL-4, IL-6, MIP-1b, KC and IL-33 expression in skin tissue and IgE expression in blood serum when a house dust mite-induced atopic dermatitis model is administered with Compound 1 at varying concentrations.

After inducing atopic dermatitis using house dust mite cream, symptoms as well as the state of the skin of the ears and backs were scored twice weekly starting from the initial date of administration; the measurements were added and the means are shown in FIG. 9. Furthermore, on the date of termination of the experiment, skin tissue and serum were collected to observe the level of expression of inflammatory cytokines in the tissue and the level of expression of IgE in serum using ELISA analysis; the results are shown in FIG. 10.

In the results, dermatitis on the back and ears was alleviated in a concentration-dependent manner for administration of Compound 1, and administration at 30 mpk was most effective at alleviating dermatitis; it was confirmed that Compound 1 was more effective at alleviating atopic dermatitis than the upadacitinib control group. Aggravation of atopic dermatitis leads to increased inflammatory cytokines that induce inflammation in the lesion area, and comparing the degree of inflammatory cytokine expression in the back tissue in the group administered Compound 1 at 30 mpk against the control group, a statistically significant reduction was confirmed. Furthermore, it is reported that IgE in serum increases if atopic dermatitis is induced in a house dust mite cream-induced atopic dermatitis model, and in the group administered Compound 1, a concentration-dependent reduction in IgE expression was confirmed, with a statistically significant reduction observed in the group administered at 30 mpk. From the above results, it can be confirmed that Compound 1 has a therapeutic effect on atopic dermatitis.

Example 9. Evaluation of In-Vivo Stability and Bioavailability of the Compounds According to the Present Invention To evaluate the in-vivo stability and bioavailability of Compound 1 according to the present invention for use as a drug, metabolic stability evaluation, a metabolic enzyme CYP inhibition assay, hERG analysis, CaCo-2 analysis to observe biomembrane permeability of the drug, and plasma stability evaluation were carried out. The results are shown in Table 5 below. MS is an index of in-vivo metabolic stability, and values confirmed that Compound 1 is safe in mice up to dogs, which are larger animals.

DDI (Drug Interaction) can be observed in a CYP inhibition assay. A luminescence assay was used to measure and evaluate inhibition activity against 1A2, 2C9, 2C19, 2D6 and 3A4, which are important Phase 1 drug metabolism CYP450 enzymes involved in drug metabolism. Whereas the CYP 3A4 index is normally suppressed, almost no enzyme inhibition activity was exhibited by the compound of the present invention.

The hERG analysis is used as an indicator of cardiac toxicity, and generally a value of 5 μM indicates safety; the compound of the present invention was confirmed to have excellent safety in terms of cardiac toxicity.

Caco-2 permeability observes the cell membrane permeability of a drug, and can be considered an index associated with drug absorption and excretion. An ER ratio value close to "1" indicates almost equivalent drug absorption and excretion, and the compound of the present invention, exhibiting a value of 1.08, was confirmed to have excellent cell membrane permeability.

Hydrolysis in plasma is a factor which, together with metabolic reactions, impacts fast in-vivo decomposition of a drug and short half-life thereof; plasma stability is a test which assesses these. The compound at a certain concentration was added to plasma and reacted for a certain period, then collected, and LC-MS/MS was used to measure the percentage of compound remaining relative to the amount prior to the reaction.

Even after 2 hours, 97.2% of the compound of the present invention remained in plasma without being degraded, and thus exhibited excellent plasma stability.

TABLE 5

| Cmpd | MS (1 µM) (% remaining during 30 min) | | | | | CYP (10 µM) (% of control activity) | | | | | hERG IC50 (µM) | Caco-2 permeability (ER ratio) | Plasma stability (% remaining, 30 and 120 min) |
| --- | --- | --- | --- | --- | --- | --- | --- | --- | --- | --- | --- | --- | --- |
| | Human | Mouse | Rat | Dog | Monkey | 1A2 | 2C9 | 2C19 | 2D6 | 3A4 | | | |
| 1 | 39 | 40 | 20 | 96 | — | 86 | 74 | 84 | 92 | 72 | 4.39 | 0.201 (1.08) | 100, 97.2 |

Example 10. Evaluation of Topical Anti-Inflammatory Activity of Compound 1 in the Imiquimod (IMQ)-Induced Psoriasis-Like Skin Inflammation Compound 1 (0.3%, 1% and 3%) and the vehicle (5% DMSO/75% PEG400/20% EtOH) were topically administered at 20 µL/mouse on the right ear once daily (QD) for 9 consecutive days. Dexamethasone (0.15%), the reference compound, was applied topically at 20 µL/mouse on the right ear once daily (QD) during the same study period.

Fifteen (15) mg imiquimod (IMQ) cream (5%) (Aldara; 3M Pharmaceuticals) was topically administered once daily (QD) on the right ear one hour after treatment from Day 1 to Day 9 for 9 consecutive days, translating to a daily dose of 0.75 mg of the active compound.

Ear swelling was measured on Day 0 and thereafter 30 min before dosing on Days 2, 4, 6 and 8. On Day 10, ear swelling was measured 24 hours after the last dosing.

Figure 11A:
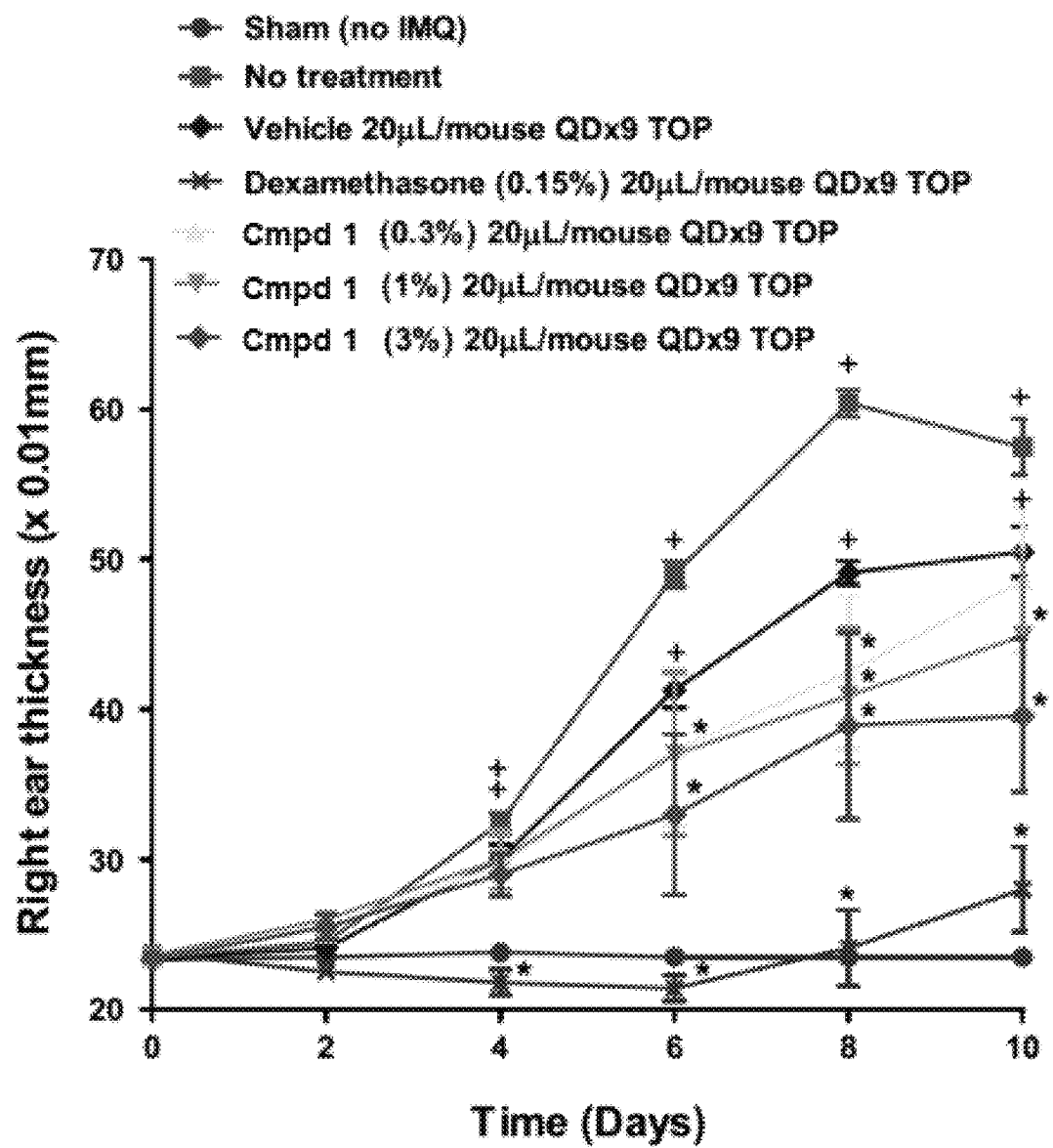
FIG. 11a and FIG. 11b show the results of the topical anti-inflammatory activity of Compound 1 in the imiquimod (IMQ)-induced psoriasis-like skin inflammation model.
Figure 11B:
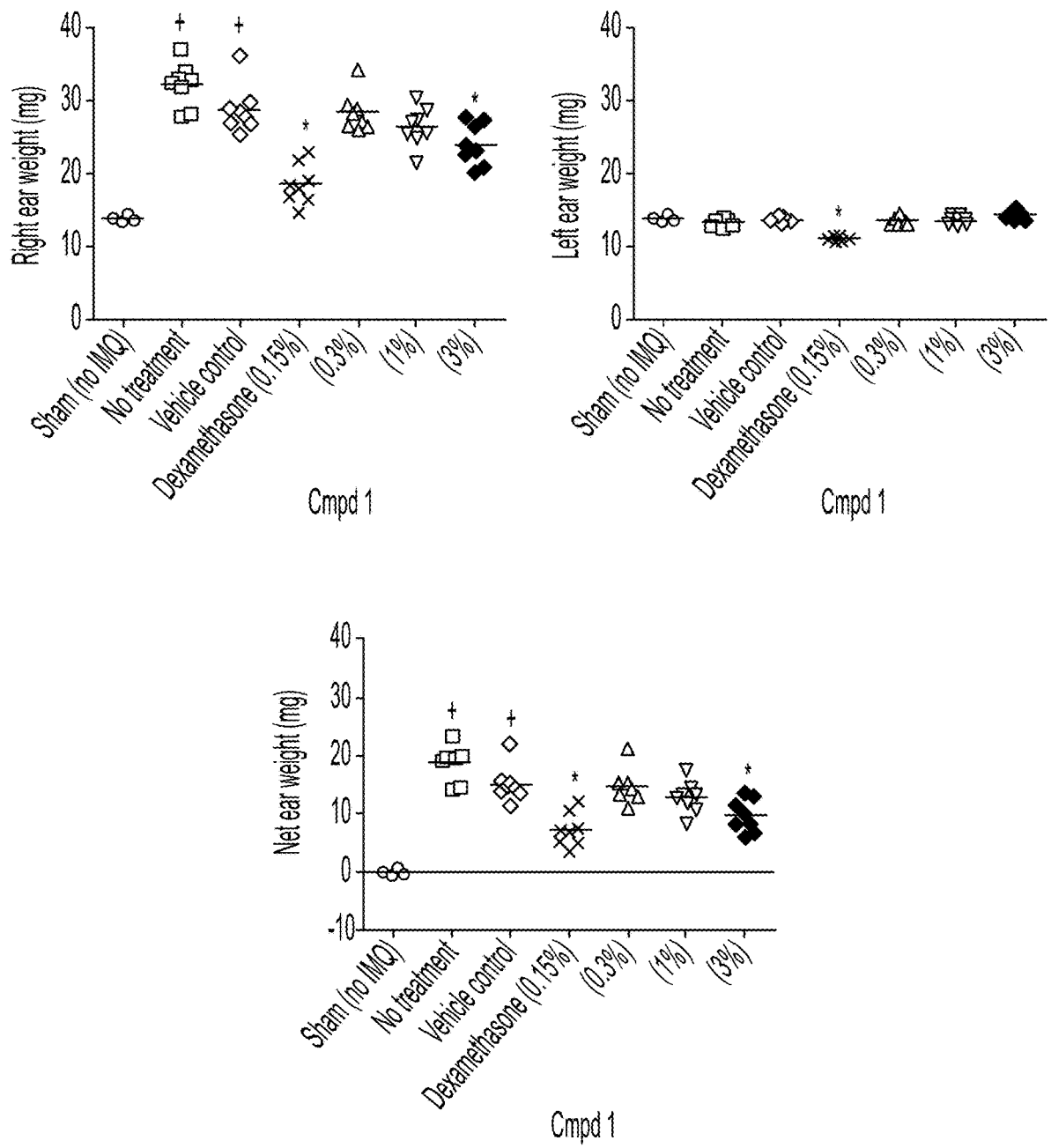

The results are shown in FIG. 11a and FIG. 11b. Topical application of mouse ear with 5% IMQ cream, a TLR7/8 ligand and potent immune activator, triggered a psoriasis-like inflammation and showed a significant (p<0.05) increase in ear swelling compared to the sham control, indicating a successful induction of IMQ-induced psoriasis in no treatment group. However, topical administration of vehicle control (5% DMSO/75% PEG400/20% EtOH) was associated with a significant (p<0.05) reduction of IMQ-induced ear swelling from Day 6 to Day 10, when compared to the no treatment group.

Compound 1 (0.3, 1% and 3%) had moderate to significant (p<0.05) inhibition on IMQ-induced ear swelling from Day 6 to Day 10 in a dose-dependent manner, relative to the no treatment and vehicle control groups. The reference compound, dexamethasone (0.15%), significantly (p<0.05) reduced the IMQ-induced ear swelling in BALB/c mice.

No significant differences in the thickness of left ear were observed between no treatment and vehicle control groups, but topical administrations of dexamethasone (0.15%) also caused significant (p<0.05) decreases in left ear swelling during the study period. The ear weight measurements were consistent with the net swelling measurements. Body weight gain between the vehicle control and treated groups were similar, only dexamethasone showed significant (p<0.05) decrease in body weight during the study period.

Per histopathological examination of the ear skin, epidermal hyperplasia, multifocal to diffuse inflammatory cell infiltration, multifocal necrosis and epidermal hyperkeratosis lesions were observed in the no treatment group and vehicle control groups. The severity of skin lesions was attenuated significantly by dexamethasone (0.15%), and Compound 1 (3%), when compared to the no treatment group and vehicle group.

In conclusion, Compound 1 (3%, high dose) at 20 µL/mouse QD×9 days given topically had significant (p<0.05) protective effects in IMQ-induced psoriasis-like inflammation, as evidenced by the improvements in ear swelling, ear weight and histopathological result in IMQ induced psoriasis model in BALB/c mice.

Example 11. Evaluation of Oral Anti-Inflammatory Activity of the Compounds in the Imiquimod (IMQ)-Induced Psoriasis-Like Skin Inflammation Compound 1 at 45 and 60 mg/kg and the vehicle (0.5% citric acid+20% HP-b-CD in DDW) at 5 mL/kg were given by oral gavage twice (BID) daily for 9 consecutive days. The positive control, methotrexate at 2 mg/kg and tofacitinib at 5 mg/kg were administered by oral gavage twice (BID) daily during the same study period.

Fifteen (15) mg Imiquimod (IMQ) cream (5%) (Aldara; 3M Pharmaceuticals) was topically (TOP) administered once daily (QD) on the right ear one hour after treatment from Day 1 to Day 9 for 9 consecutive days, translating to a daily dose of 0.75 mg of the active compound. Ear swelling was measured on Day 0 and thereafter 30 min before dosing on Days 2, 4, 6 and 8. On Day 10, ear swelling was measured 24 hours after the last dosing.

Figure 12A:
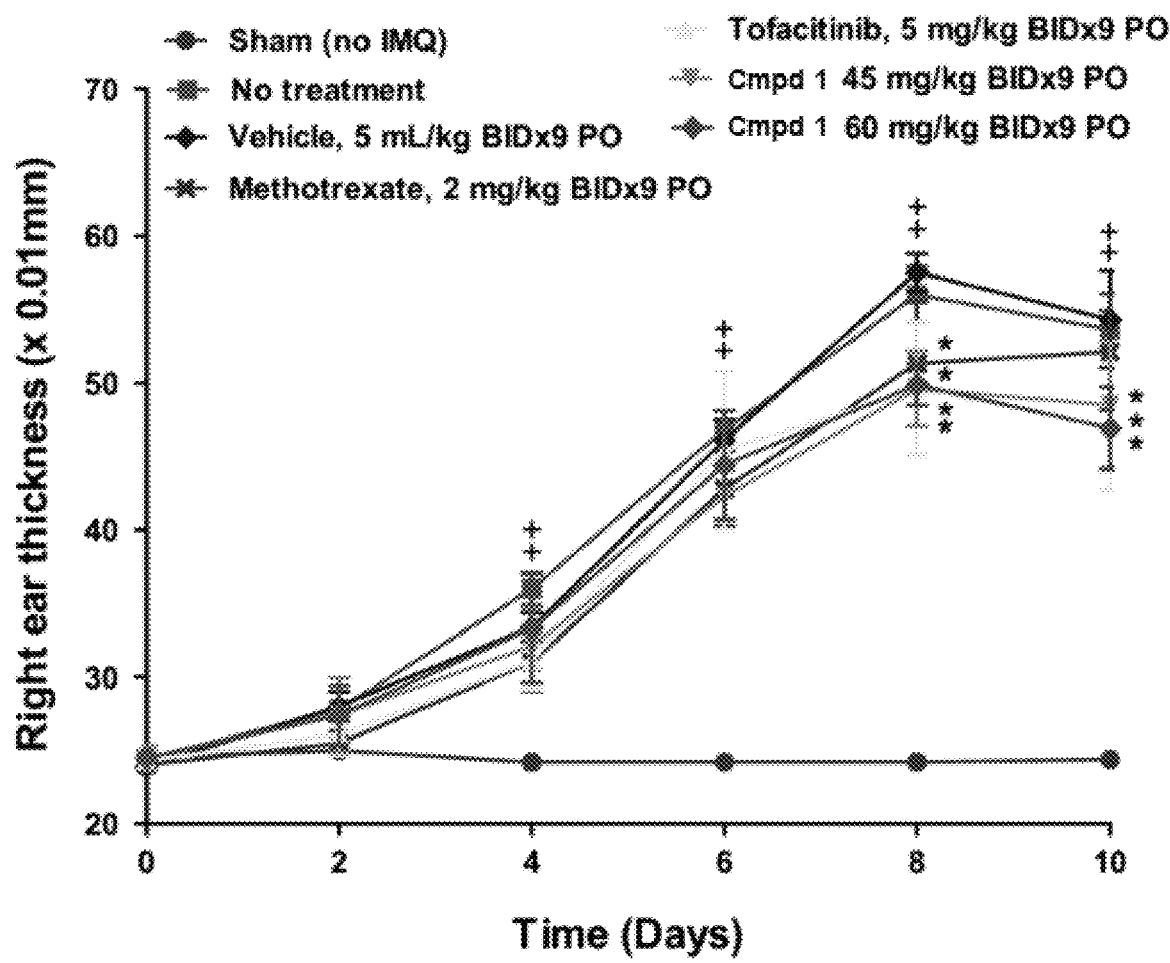
FIG. 12a and FIG. 12b show the results of the oral anti-inflammatory activity of Compound 1 in the imiquimod (IMQ)-induced psoriasis-like skin inflammation model.
Figure 12B:
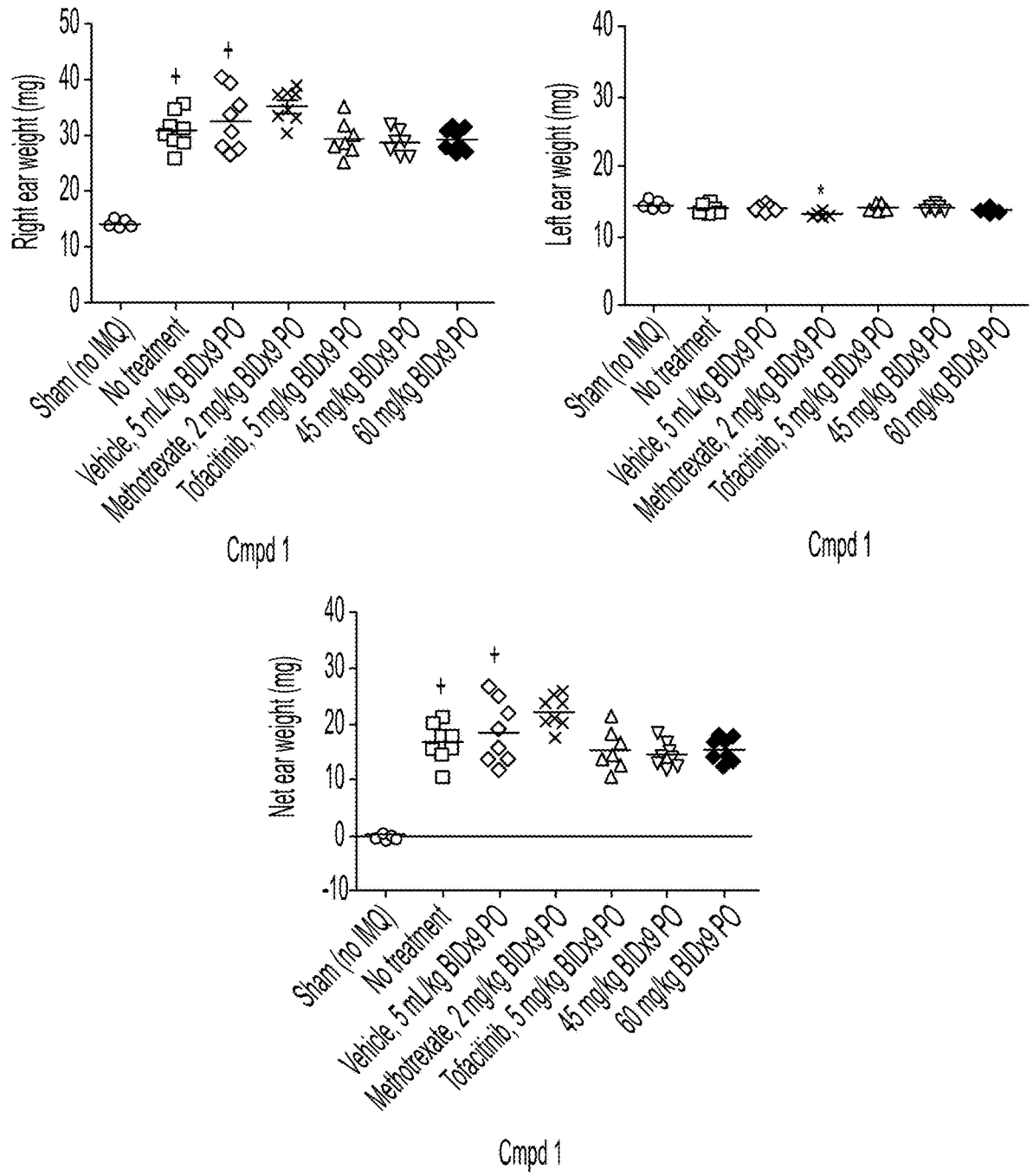

The results are shown in FIG. 12a and FIG. 12b. Topical application on mouse ear with 5% IMQ cream, a TLR7/8 ligand and potent immune activator, triggered a psoriasis-like inflammation and showed a significant (p<0.05) increase in ear swelling compared to the sham control, indicating a successful induction of IMQ-induced psoriasis in both no treatment and vehicle control (0.5% citric acid+ 20% HP-b-CD in DDW) groups.

Compound 1 given at 45 and 60 mg/kg had a statistically (p<0.05) significant inhibition on IMQ-induced ear swelling from Day 8 to Day 10, when compared to the vehicle group.

The positive control, methotrexate at 2 mg/kg showed a significant (p<0.05) effect on the IMQ-induced ear swelling on Day 8, when compared to the vehicle group. Tofacitinib given at 5 mg/kg also showed a significant (p<0.05) inhibition on IMQ-induced ear swelling from Day 8 to Day 10 in the study.

All treated groups showed a little, but significant difference in the thickness of left ear, when compared to the vehicle group during the study period. The ear weight measurements were consistent with the net swelling measurements.

Body weight gain between the vehicle control and treated groups were comparable during the study period. However, methotrexate at 2 mg/kg PO BID×9 days significantly decreased the body weight from Day 9 to Day 10 in the study.

In conclusion, Compound 1 at 45 and 60 mg/kg PO BID×9 days had significantly (p<0.05) protective effects on IMQ-induced psoriasis-like inflammation, as evidenced by the improvement in ear swelling in IMQ induced psoriasis model in BALB/c mice.

While we have described a number of embodiments of this invention, it is apparent that our basic examples may be altered to provide other embodiments that utilize the compounds and methods of this invention. Therefore, the scope of this invention is to be defined by the appended claims rather than by the specific embodiments that have been represented by way of example.

The invention claimed is:

1. A method of treating an inflammatory disease in a patient in need thereof, the method comprising administering to the patient a compound represented by Chemical Formula 1:

[Chemical Formula 1]

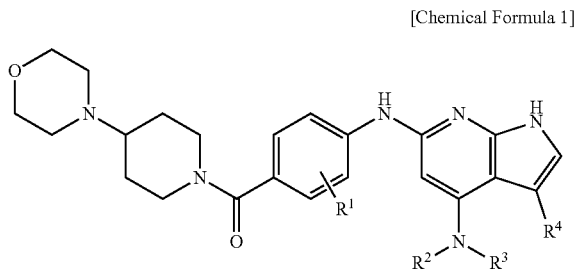

or an isomer, pharmaceutically acceptable salt, or pharmaceutical composition thereof, wherein:
$R^1$ is $C_1$-$C_3$ alkoxy;
$R^2$ and $R^3$ are each independently hydrogen, straight chain or branched chain $C_1$-$C_{10}$ alkyl, or $C_3$-$C_6$ cycloalkyl; and
$R^4$ is haloalkyl,
wherein the inflammatory disease is selected from arthritis, inflammatory bowel disease, atopic dermatitis, psoriasis, autoimmune disease and colitis.

2. The method of claim 1, wherein the method of treating an inflammatory disease comprises one or more of:
(a) reducing pro-inflammatory cytokines in the patient;
(b) increasing differentiation of regulatory T cells ($T_{reg}$) in the patient; and
(c) decreasing pro-inflammatory T cells in the patient.

3. A method of reducing pro-inflammatory cytokines in a patient in need thereof, the method comprising administering to the patient a compound represented by Chemical Formula 1:

[Chemical Formula 1]

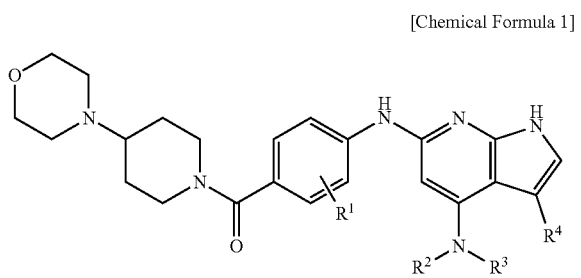

or an isomer, pharmaceutically acceptable salt, or pharmaceutical composition thereof, wherein:
$R^1$ is $C_1$-$C_3$ alkoxy;
$R^2$ and $R^3$ are each independently hydrogen, straight chain or branched chain $C_1$-$C_{10}$ alkyl, or $C_3$-$C_6$ cycloalkyl; and
$R^4$ is haloalkyl.

4. The method of claim 2, wherein the pro-inflammatory cytokine is selected from one or more of NO, IFN-γ, IL-1α, IL-1β, IL-4, IL-6, IL-10, IL-12, IL-13, IL-17, IL-17A, IL-22, IL-23, KC, MIP-1a, MIP-1b, GM-CSF, and TNF-α.

5. A method of increasing differentiation of regulatory T cells ($T_{reg}$) in a patient in need thereof, the method comprising administering to the patient a compound represented by Chemical Formula 1:

[Chemical Formula 1]

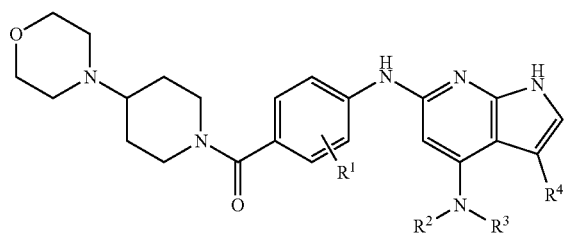

or an isomer, pharmaceutically acceptable salt, or pharmaceutical composition thereof, wherein:
$R^1$ is $C_1$-$C_3$ alkoxy;
$R^2$ and $R^3$ are each independently hydrogen, straight chain or branched chain $C_1$-$C_{10}$ alkyl, or $C_3$-$C_6$ cycloalkyl; and
$R^4$ is haloalkyl.

6. A method of decreasing pro-inflammatory T cells in a patient in need thereof, the method comprising administering to the patient a compound represented by Chemical Formula 1:

[Chemical Formula 1]

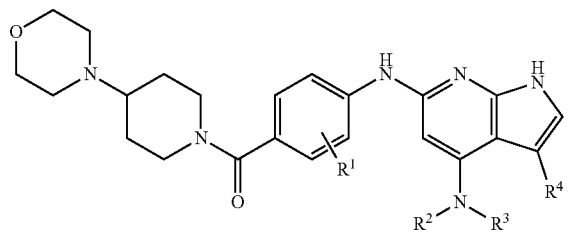

or an isomer, pharmaceutically acceptable salt, or pharmaceutical composition thereof, wherein:
$R^1$ is $C_1$-$C_3$ alkoxy;
$R^2$ and $R^3$ are each independently hydrogen, straight chain or branched chain $C_1$-$C_{10}$ alkyl, or $C_3$-$C_6$ cycloalkyl; and
$R^4$ is haloalkyl.

7. The method of claim 2, wherein the pro-inflammatory T cells are Th17.

8. The method of claim 1, wherein $R^1$ is methoxy.

9. The method of claim 1, wherein, $R^2$ is a straight chain or branched chain $C_1$-$C_5$ alkyl.

10. The method of claim 1, wherein, $R^2$ is a $C_3$-$C_4$ cycloalkyl.

11. The method of claim 1, wherein, $R^3$ is hydrogen.

12. The method of claim 1, wherein, $R^4$ is trifluoromethyl.

13. The method of claim 1, wherein the compound represented by Chemical Formula 1 is:
(1) (4-((-4-ethylamino)-3-(trifluoromethyl)-1H-pyrrolo[2,3-b]pyridine-6-yl)amino)-3-methoxyphenyl)(4-morpholinopiperidine-1-yl) methanone;
(2) (3-methoxy-4-((4-(methylamino)-3-(trifluoromethyl)-1H-pyrrolo[2.3-b]pyridine-6-yl)amino)phenyl)(4-morpholinopiperidine-1-yl)methanone;

(3) (4-(4-(isopropylamino)-3-(trifluoromethyl)-1H-pyrrolo[2,3-b]pyridine-6-ylamino)-3-methoxyphenyl)(4-morpholinopiperidine-1-yl)methanone;
(4) (S)-(4-((4-(2-butylamino)-3-(trifluoromethyl)-1H-pyrrolo[2,3-b]pyridin-6-yl)amino)-3-methoxyphenyl)(4-morpholinopiperidine-1-yl)-methanone; or
(5) (4-((4-(cyclopropylamino)-3-(trifluoromethyl)-1-((2-(trimethylsilyl)ethoxy)methyl)-1H-pyrrolo[2,3-b]pyridine-6-yl)3-methoxyphenyl) (4-morpholinopiperidine-1-yl)methanone.

14. The method of claim 1, wherein the compound represented by Chemical Formula 1 is (4-((-4-ethylamino)-3-(trifluoromethyl)-1H-pyrrolo[2,3-b]pyridine-6-yl)amino)-3-methoxyphenyl)(4-morpholinopiperidine-1-yl) methanone.

15. The method of claim 1, wherein the compound represented by Chemical Formula 1 inhibits protein kinase activity.

16. The method of claim 1, wherein the method comprises conjointly administering a compound represented by Chemical Formula 1, or an isomer, pharmaceutically acceptable salt, or pharmaceutical composition thereof and at least one additional active ingredient.

17. The method of claim 16, wherein at least one additional active ingredient is selected from gamma globulin, phosphodiesterase inhibitors, IRAK4 inhibitors, belimumab, tacrolimus, rapamycin, mycophenolate mofetil, interferon, paracetamol, acetaminophen, non-steroidal anti-inflammatory drugs, corticosteroids, probenecid, allopurinol, febuxostat, sulfasalazinc, antimalarials, methotrexate, gold salts, D-penicillamine, azathioprine, cyclophosphamide, chlorambucil, cyclosporine, leflunomide, "anti-TNF" agents, "anti-IL-1" agents, canakinumab, anti-JAK/STAT inhibitors, antibodies, "anti-T-cell" agents, "anti-IL-6" agents, monoclonal antibodies, anticoagulants, antidiarrheals, bile acid binding agents, laxatives, anticholinergics or antispasmodics, beta-2 agonists, anticholinergic agents, inhaled corticosteroids, methylxanthines, IgE antibodies, nucleoside reverse transcriptase inhibitors, non-nucleoside reverse transcriptase inhibitors, nucleotide reverse transcriptase inhibitors, protease inhibitors, entry inhibitors, integrase inhibitors, or any combination(s) thereof.

18. The pharmaceutical composition of claim 1, further comprising excipients, disintegrating agents, sweetening agents, lubricants, and/or flavoring agents.

19. The method of claim 3, wherein $R^1$ is methoxy.
20. The method of claim 3, wherein $R^2$ is a straight chain or branched chain $C_1$-$C_5$ alkyl.
21. The method of claim 3, wherein $R^2$ is a $C_3$-$C_4$ cycloalkyl.
22. The method of claim 3, wherein $R^3$ is hydrogen.
23. The method of claim 3, wherein $R^4$ is trifluoromethyl.
24. The method of claim 3, wherein the compound represented by Chemical Formula 1 is:
(1) (4-((-4-ethylamino)-3-(trifluoromethyl)-1H-pyrrolo[2,3-b]pyridine-6-yl) amino)-3-methoxyphenyl)(4-morpholinopiperidine-1-yl) methanone;
(2) (3-methoxy-4-((4-(methylamino)-3-(trifluoromethyl)-1H-pyrrolo[2,3-b] pyridine-6-yl) amino)phenyl)(4-morpholinopiperidine-1-yl) methanone;
(3) (4-(4-(isopropylamino)-3-(trifluoromethyl)-1H-pyrrolo[2,3-b]pyridine-6-ylamino)-3-methoxyphenyl)(4-morpholinopiperidine-1-yl)methanone;
(4) (S)-(4-((4-(2-butylamino)-3-(trifluoromethyl)-1H-pyrrolo[2,3-b]pyridin-6-yl)amino)-3-methoxyphenyl) (4-morpholinopiperidine-1-yl)-methanone; or
(5) (4-((4-(cyclopropylamino)-3-(trifluoromethyl)-1-((2-(trimethylsilyl)ethoxy)methyl)-1H-pyrrolo[2,3-b] pyridine-6-yl)3-methoxyphenyl) (4-morpholinopiperidine-1-yl) methanone.

25. The method of claim 3, wherein the compound represented by Chemical Formula 1 is (4-((-4-ethylamino)-3-(trifluoromethyl)-1H-pyrrolo[2,3-b]pyridine-6-yl)amino)-3-methoxyphenyl)(4-morpholinopiperidine-1-yl) methanone.

26. The method of claim 5, wherein $R^1$ is methoxy.
27. The method of claim 5, wherein, $R^2$ is a straight chain or branched chain $C_1$-$C_5$ alkyl.
28. The method of claim 5, wherein, $R^2$ is a $C_3$-$C_4$ cycloalkyl.
29. The method of claim 5, wherein, $R^3$ is hydrogen.
30. The method of claim 5, wherein, $R^4$ is trifluoromethyl.
31. The method of claim 5, wherein the compound represented by Chemical Formula 1 is:
(1) (4-((-4-ethylamino)-3-(trifluoromethyl)-1H-pyrrolo[2,3-b]pyridine-6-yl)amino)-3-methoxyphenyl)(4-morpholinopiperidine-1-yl)methanone;
(2) (3-methoxy-4-((4-(methylamino)-3-(trifluoromethyl)-1H-pyrrolo[2,3-b] pyridine-6-y1)amino)phenyl)(4-morpholinopiperidine-1-yl)methanone;
(3) (4-(4-(isopropylamino)-3-(trifluoromethyl)-1H-pyrrolo[2,3-b]pyridine-6-ylamino)-3-methoxyphenyl)(4-morpholinopiperidine-1-yl)methanone;
(4) (S)-(4-((4-(2-butylamino)-3-(trifluoromethyl)-1H-pyrrolo[2,3-b]pyridin-6-yl)amino)-3-methoxyphenyl) (4-morpholinopiperidine-1-yl)-methanone; or
(5) (4-((4-(cyclopropylamino)-3-(trifluoromethyl)-1-((2-(trimethylsilyl)ethoxy)methyl)-1H-pyrrolo[2,3-b] pyridine-6-yl)3-methoxyphenyl) (4-morpholinopiperidine-1-yl)methanone.

32. The method of claim 5, wherein the compound represented by Chemical Formula 1 is (4-((-4-ethylamino)-3-(trifluoromethyl)-1H-pyrrolo[2,3-b]pyridine-6-yl)amino)-3-methoxyphenyl)(4-morpholinopiperidine-1-yl)methanone.

33. The method of claim 6, wherein $R^1$ is methoxy.
34. The method of claim 6, wherein $R^2$ is a straight chain or branched chain $C_1$-$C_5$ alkyl.
35. The method of claim 6, wherein $R^2$ is a $C_3$-$C_4$ cycloalkyl.
36. The method of claim 6, wherein $R^3$ is hydrogen.
37. The method of claim 6, wherein $R^4$ is trifluoromethyl.
38. The method of claim 6, wherein the compound represented by Chemical Formula 1 is:
(1) (4-((-4-ethylamino)-3-(trifluoromethyl)-1H-pyrrolo[2,3-b]pyridine-6-yl)amino)-3-methoxyphenyl)(4-morpholinopiperidine-1-yl)methanone;
(2) (3-methoxy-4-((4-(methylamino)-3-(trifluoromethyl)-1H-pyrrolo[2,3-b] pyridine-6-yl)amino)phenyl)(4-morpholinopiperidine-1-yl)methanone;
(3) (4-(4-(isopropylamino)-3-(trifluoromethyl)-1H-pyrrolo[2,3-b]pyridine-6-ylamino)-3-methoxyphenyl)(4-morpholinopiperidine-1-yl)methanone;
(4) (S)-(4-((4-(2-butylamino)-3-(trifluoromethyl)-1H-pyrrolo[2,3-b]pyridin-6-yl)amino)-3-methoxyphenyl) (4-morpholinopiperidine-1-yl)-methanone; or
(5) (4-((4-(cyclopropylamino)-3-(trifluoromethyl)-1-((2-(trimethylsilyl)ethoxy)methyl)-1H-pyrrolo[2,3-b] pyridine-6-yl)3-methoxyphenyl)(4-morpholinopiperidine-1-yl) methanone.

39. The method of claim 6, wherein the compound represented by Chemical Formula 1 is (4-((-4-ethylamino)-

3-(trifluoromethyl)-1H-pyrrolo[2,3-b]pyridine-6-yl)amino)-3-methoxyphenyl)(4-morpholinopiperidine-1-yl) methanone.

\* \* \* \* \*

UNITED STATES PATENT AND TRADEMARK OFFICE
CERTIFICATE OF CORRECTION

| | | |
|---|---|---|
| PATENT NO. | : 12,194,048 B2 | Page 1 of 3 |
| APPLICATION NO. | : 18/486783 | |
| DATED | : January 14, 2025 | |
| INVENTOR(S) | : Soo Chan Kim et al. | |

It is certified that error appears in the above-identified patent and that said Letters Patent is hereby corrected as shown below:

In the Specification

Column 19, Table, 1, compound structure 4:
The following structure is incorrect:

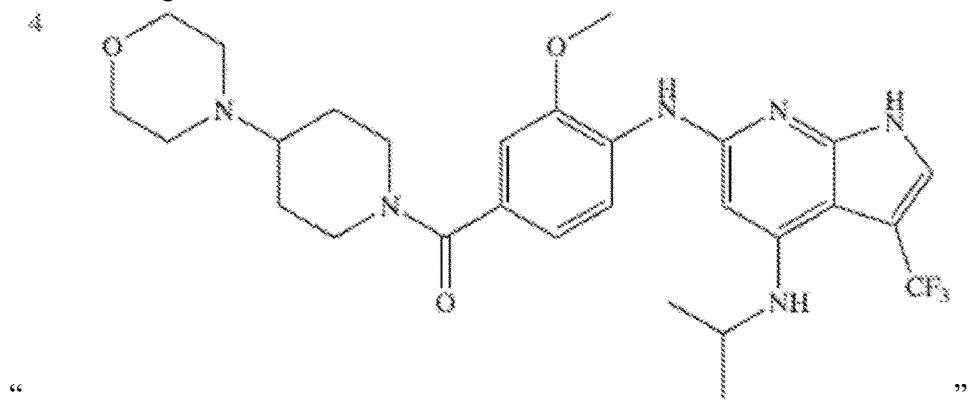

"

Should read:

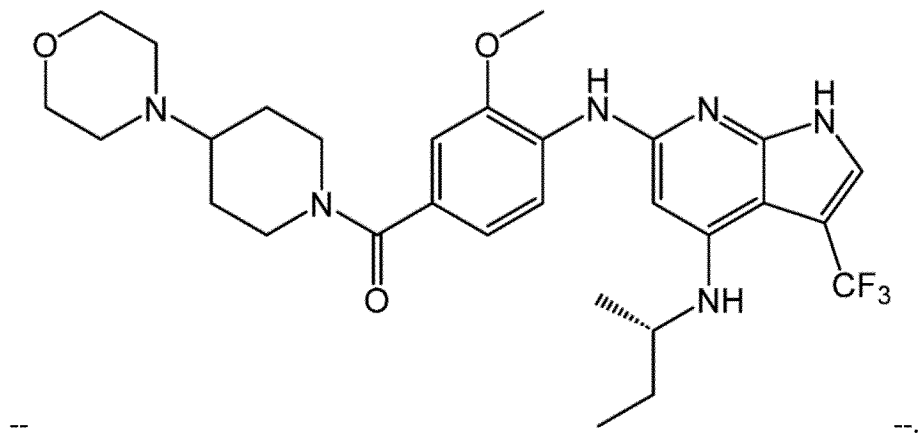

--           --.

Signed and Sealed this
Twentieth Day of May, 2025

Coke Morgan Stewart
*Acting Director of the United States Patent and Trademark Office*

Columns 19-20, compound structure 5, compound name:
"(4-((4-(cyclopropylamino )-3-(trifluoromethyl)-1-((2-(trimethylsilyl)ethoxy )methyl)- lHpyrrolo[2,3-b Jpyridine-6-yl) 3-methoxyphenyl) (4-morpholinopiperidine-1-yl)methanone"
Should read:
-- (4-((4-(cyclopropylamino)-3-(trifluoromethyl)-1H-pyrrolo[2,3-b]pyridin-6-yl)amino)-3-methoxyphenyl)(4-morpholinopiperidin-1-yl)methanone --.

In the Claims

Column 30, Claim 13, Line 66:
"[2.3-b]"
Should read:
-- [2,3-b] --.

Column 31, Claim 13, Lines 7-10:
"(5) (4-(( 4-(cyclopropylamino )-3-(trifluoromethyl)-1-((2-(trimethylsilyl)ethoxy)methyl)-1H-pyrrolo[2,3-b]pyridine-6-yl)3-methoxyphenyl) (4-morpholinopiperidine-1-yl)methanone."
Should read:
-- (5) (4-((4-(cyclopropylamino)-3-(trifluoromethyl)-1H-pyrrolo[2,3-b]pyridin-6-yl)amino)-3-methoxyphenyl)(4-morpholinopiperidin-1-yl)methanone --.

Column 31, Claim 15, Line 18:
"activity."
Should read:
-- activity in the patient. --.

Column 32, Claim 24, Lines 1-4:
"(5) (4-(( 4-(cyclopropylamino )-3-(trifluoromethyl)-1-((2-(trimethylsilyl)ethoxy)methyl)-1H-pyrrolo[2,3-b]pyridine-6-yl)3-methoxyphenyl) (4-morpholinopiperidine-1-yl)methanone."
Should read:
-- (5) (4-((4-(cyclopropylamino)-3-(trifluoromethyl)-1H-pyrrolo[2,3-b]pyridin-6-yl)amino)-3-methoxyphenyl)(4-morpholinopiperidin-1-yl)methanone --.

Column 32, Claim 31, Lines 32-35:
"(5) (4-((4-(cyclopropylamino )-3-(trifluoromethyl)-1-((2-(trimethylsilyl)ethoxy)methyl)-1H-pyrrolo[2,3-b]pyridine-6-yl)3-methoxyphenyl) (4-morpholinopiperidine-1-yl)methanone."
Should read:
-- (5) (4-((4-(cyclopropylamino)-3-(trifluoromethyl)-1H-pyrrolo[2,3-b]pyridin-6-yl)amino)-3-methoxyphenyl)(4-morpholinopiperidin-1-yl)methanone --.

Column 32, Claim 38, Line 57:
"pyridine-6-ylamino)"
Should read:
-- pyridine-6-yl)amino) --.

Column 32, Claim 38, Lines 62-65:
"(5) (4-((4-(cyclopropylamino )-3-(trifluoromethyl)-1-((2-(trimethylsilyl)ethoxy)methyl)-1H-pyrrolo[2,3-b]pyridine-6-yl)3-methoxyphenyl) (4-morpholinopiperidine-l-yl)methanone."
Should read:
-- (5) (4-((4-(cyclopropylamino)-3-(trifluoromethyl)-1H-pyrrolo[2,3-b]pyridin-6-yl)amino)-3-methoxyphenyl)(4-morpholinopiperidin-1-yl)methanone --.